(12) United States Patent
Sato et al.

(10) Patent No.: US 9,510,833 B2
(45) Date of Patent: Dec. 6, 2016

(54) APPLICATOR AND TISSUE FASTENING METHOD THROUGH NATURAL ORIFICE

(75) Inventors: Masatoshi Sato, Yokohama (JP); Kunihide Kaji, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/036,959

(22) Filed: Feb. 28, 2011

(65) Prior Publication Data
US 2011/0152886 A1 Jun. 23, 2011

Related U.S. Application Data

(63) Continuation of application No. 11/710,732, filed on Feb. 26, 2007, now abandoned.

(51) Int. Cl.
*A61B 17/11* (2006.01)
*A61B 17/115* (2006.01)
(Continued)

(52) U.S. Cl.
CPC .......... *A61B 17/1114* (2013.01); *A61B 17/115* (2013.01); *A61B 17/00234* (2013.01); *A61B 17/11* (2013.01); *A61B 2017/00867* (2013.01);
(Continued)

(58) Field of Classification Search
CPC ............ A61B 17/128; A61B 17/1285; A61B 17/122; A61B 17/1225; A61B 17/1227; A61B 17/10; A61B 17/11; A61B 17/1103; A61B 17/1107; A61B 17/1114; A61B 2017/1117; A61B 2017/1225; A61B 17/083; A61B 17/08; A61B 17/0487; A61B 2017/0488; A61B 17/081; A61B 2017/00867; A61B 2017/0649; A61B 2017/1139; A61B 2017/00575; A61B 2017/00592; A61B 2017/00584; A61B 2017/00606; A61F 2/88
USPC .......................... 606/139, 142, 143, 151, 153
See application file for complete search history.

(56) References Cited

U.S. PATENT DOCUMENTS 4,055,186 A * 10/1977 Leveen .......................... 606/153
5,246,445 A * 9/1993 Yachia ...................... A61F 2/88
604/104
(Continued)

FOREIGN PATENT DOCUMENTS

| JP | S54-145362 | 11/1979 |
|----|------------|---------|
| JP | 2003-220065 | 8/2003 |

(Continued)

OTHER PUBLICATIONS

Japanese Office Action dated Nov. 24, 2009 with English translation.
(Continued)

*Primary Examiner* — Christopher L Templeton
(74) *Attorney, Agent, or Firm* — Scully, Scott, Murphy & Presser, P.C.

(57) ABSTRACT

The applicator related to the present invention is provided with a flexible sheath longer than the overall length of an instrument channel of a flexible endoscope; an operation part used outside the instrument channel; a deployed section that can be made to protrude from the front end of the sheath by operating the operation part and to pierce a tissue; a tissue fastening tool made of a superelastic wire formed in coil shape and housed inside the deployed section in a substantially extended condition; and a pusher that pushes out the tissue fastening tool from the deployed section when the operation part is operated.

8 Claims, 33 Drawing Sheets

(51) Int. Cl.
*A61B 17/00* (2006.01)
*A61B 17/064* (2006.01)

(52) U.S. Cl.
CPC . *A61B 2017/0649* (2013.01); *A61B 2017/1117* (2013.01); *A61B 2017/1139* (2013.01)

(56) References Cited

U.S. PATENT DOCUMENTS

| | | | |
|---|---|---|---|
| 5,514,176 A * | 5/1996 | Bosley, Jr. | A61F 2/88 606/156 |
| 5,540,701 A * | 7/1996 | Sharkey et al. | 606/153 |
| 5,766,160 A * | 6/1998 | Samson | A61B 17/12022 606/1 |
| 5,782,844 A * | 7/1998 | Yoon et al. | 606/139 |
| 5,810,851 A * | 9/1998 | Yoon | 606/148 |
| 5,972,001 A * | 10/1999 | Yoon | 606/139 |
| 5,980,514 A * | 11/1999 | Kupiecki | A61B 17/12022 604/104 |
| 6,010,517 A * | 1/2000 | Baccaro | A61B 17/12022 606/151 |
| 6,113,611 A * | 9/2000 | Allen et al. | 606/151 |
| 6,171,320 B1 | 1/2001 | Monassevitch | 606/151 |
| 6,171,338 B1 * | 1/2001 | Talja | A61B 17/11 623/1.22 |
| 6,375,671 B1 * | 4/2002 | Kobayashi et al. | 606/213 |
| 6,402,765 B1 * | 6/2002 | Monassevitch et al. | 606/151 |
| 6,616,675 B1 * | 9/2003 | Evard | A61B 1/3137 606/153 |
| 6,709,442 B2 | 3/2004 | Miller et al. | |
| 6,790,218 B2 * | 9/2004 | Jayaraman | 606/191 |
| 6,837,893 B2 * | 1/2005 | Miller | 606/139 |
| 6,884,248 B2 * | 4/2005 | Bolduc et al. | 606/143 |
| 6,896,684 B2 | 5/2005 | Monassevitch et al. | |
| 6,986,784 B1 * | 1/2006 | Weiser et al. | 623/1.1 |
| 7,077,850 B2 * | 7/2006 | Kortenbach | 606/151 |
| 7,618,427 B2 * | 11/2009 | Ortiz et al. | 606/142 |
| 7,879,047 B2 * | 2/2011 | Ho et al. | 606/142 |
| 8,021,374 B2 * | 9/2011 | Bica-Winterling et al. | 606/142 |
| 8,109,946 B2 * | 2/2012 | Cahill et al. | 606/151 |
| 2002/0010481 A1 * | 1/2002 | Jayaraman | 606/151 |
| 2002/0173742 A1 * | 11/2002 | Keren | A61B 17/00234 604/9 |
| 2004/0098043 A1 * | 5/2004 | Trout, III | 606/213 |
| 2004/0220596 A1 * | 11/2004 | Frazier et al. | 606/153 |
| 2005/0131429 A1 | 6/2005 | Ho et al. | |
| 2005/0143763 A1 * | 6/2005 | Ortiz et al. | 606/153 |
| 2005/0177246 A1 * | 8/2005 | Datta | A61F 2/88 623/23.7 |
| 2005/0187568 A1 * | 8/2005 | Klenk | A61B 17/0057 606/153 |
| 2005/0267495 A1 | 12/2005 | Ginn et al. | |
| 2006/0095058 A1 * | 5/2006 | Sivan | A61B 17/08 606/170 |
| 2006/0212047 A1 * | 9/2006 | Abbott et al. | 606/142 |
| 2007/0055333 A1 * | 3/2007 | Forde et al. | 607/119 |
| 2007/0073315 A1 * | 3/2007 | Ginn et al. | 606/151 |
| 2007/0083226 A1 * | 4/2007 | Buiser | A61B 17/12022 606/200 |
| 2007/0083235 A1 * | 4/2007 | Jervis | A61B 17/0401 606/232 |
| 2008/0004640 A1 * | 1/2008 | Ellingwood | 606/151 |
| 2008/0051626 A1 * | 2/2008 | Sato et al. | 600/101 |
| 2010/0099947 A1 * | 4/2010 | Sato et al. | 600/104 |

FOREIGN PATENT DOCUMENTS

| | | |
|---|---|---|
| JP | 2005-177780 | 7/2005 |
| JP | 2005-193044 | 7/2005 |
| JP | 2006-101915 | 4/2006 |
| WO | WO 00/16701 | 3/2000 |
| WO | WO 02/19923 A1 | 3/2002 |
| WO | WO 2004/004579 A1 | 1/2004 |
| WO | WO 2006/098155 A1 | 9/2006 |
| WO | WO 2007/005996 A2 | 1/2007 |

OTHER PUBLICATIONS

Japanese Notice of Allowance dated Feb. 16, 2010 with English translation.
Partial European Search Report dated Mar. 3, 2010.

* cited by examiner $d_2 > d_1$

US 9,510,833 B2

APPLICATOR AND TISSUE FASTENING METHOD THROUGH NATURAL ORIFICE

CROSS REFERENCE TO RELATED APPLICATION

This application is a continuation application of U.S. application Ser. No. 11/710,732 filed on Feb. 26, 2007, now abandoned, the entire contents of which is incorporated herein by reference.

BACKGROUND OF THE INVENTION

Field of the Invention

The present invention relates to an applicator and tissue fastening method to perform the procedure for fastening tissues through a natural orifice.

Description of Related Art

Transcutaneous insertion of medical instruments as a treatment of body organs is well known. This method is less invasive compared to incising the abdomen, and quick recovery is anticipated.

A medical instrument used for transcutaneous procedures has a shaft made of hard material inserted in the body transcutaneously, with a forceps and so on provided at the front end of the shaft. For instance, a treatment instrument used in applications such as connecting hollow organs is disclosed in Japanese Unexamined Patent Application, First Publication No. 2005-193044. This intraluminal anastomosis device has a grasper fitted to the front end of the shaft that can freely open and close, and an anastomosis clamp inserted in the shaft. The anastomosis clamp can be pushed out from the front end of the shaft by the protruding device located at proximally to the operator. The anastomosis clamp is formed by annealing shape memory alloy into flat coil shape and inserting it in the shaft in the elongated condition. When the anastomosis clamp is used, the clamp is pushed out from the protruding device and inserted into the body. The surgical clamp is heated by body temperature and restored to its original coil shape. The hollow organs are joined by the restored anastomosis clamp.

Other examples of dispensing the anastomosis clamp are disclosed in the international publication number WO2002/019923. Here, the anastomosis clamp is pushed out from the needle and dispensed to the tissue. For this reason, a stopper is provided to control the depth to which the needle pierces the tissue and the amount of the anastomosis clamp is dispensed into the tissue. When performing the procedure, the instrument containing the anastomosis clamp and the needle is deployed to the tissue. The needle is advanced to pierce the layers of tissue, and the position of the anastomosis clamp is fixed by the stopper. Thereafter, the needle is pulled out of the tissue. The anastomosis clamp does not move because of the stopper; therefore, its front end part remains inside of the inside layer. When the instrument is removed from the tissue, the rest of the anastomosis clamp remains outside of the outside layer. When the coil shape of the anastomosis clamp is restored, the layers of the tissue are anastomosed.

SUMMARY OF THE INVENTION

The main object of the present invention is to fasten tissues through a natural orifice in comparison to the conventional procedures of fixing tissues transcutaneously so that invasiveness is reduced further and quick recovery can be anticipated.

The applicator related to the first aspect of the present invention is provided with: a flexible sheath longer than the overall length of an instrument channel of a flexible endoscope; an operation part used outside the instrument channel; a deployed section that can be made to protrude from the front end of the sheath by operating the operation part and to pierce tissues; a tissue fastening tool made of a superelastic wire formed in coil shape and housed inside the deployed section in a substantially extended condition; and a pusher that pushes out the tissue fastening tool from the deployed section when the operation part is operated.

The tissue fastening method through a natural orifice related to the second aspect of the present invention includes: inserting a deployed section housed in a substantially extended condition in a tissue fastening tool made of a superelastic wire formed in coil shape into the body through a flexible endoscope; piercing the deployed section into a tissue to be fastened; penetrating a tissue with a part of the tissue fastening tool housed in the deployed section and thereafter pushing it out of the deployed section to restore its original coil shape; and pulling out the deployed section from the tissue and thereafter pushing out the remaining part of the tissue fastening tool to restore its original coil shape.

The method of manufacture of double coil spring related to the third aspect of the present invention includes: winding an element wire on the core; covering the element wire wound on the core by a spacer with a slit; pulling out the element wire from the slit to the outer periphery of the spacer and winding the element wire around the periphery of the spacer; and heat treating the element wire wound over the core and the spacer.

DETAILED DESCRIPTION OF THE INVENTION

Embodiments are described here. The same reference numbers are affixed to the same elements in each mode of the embodiments. Duplication of explanations is omitted.

(First Embodiment)

Figure 1:
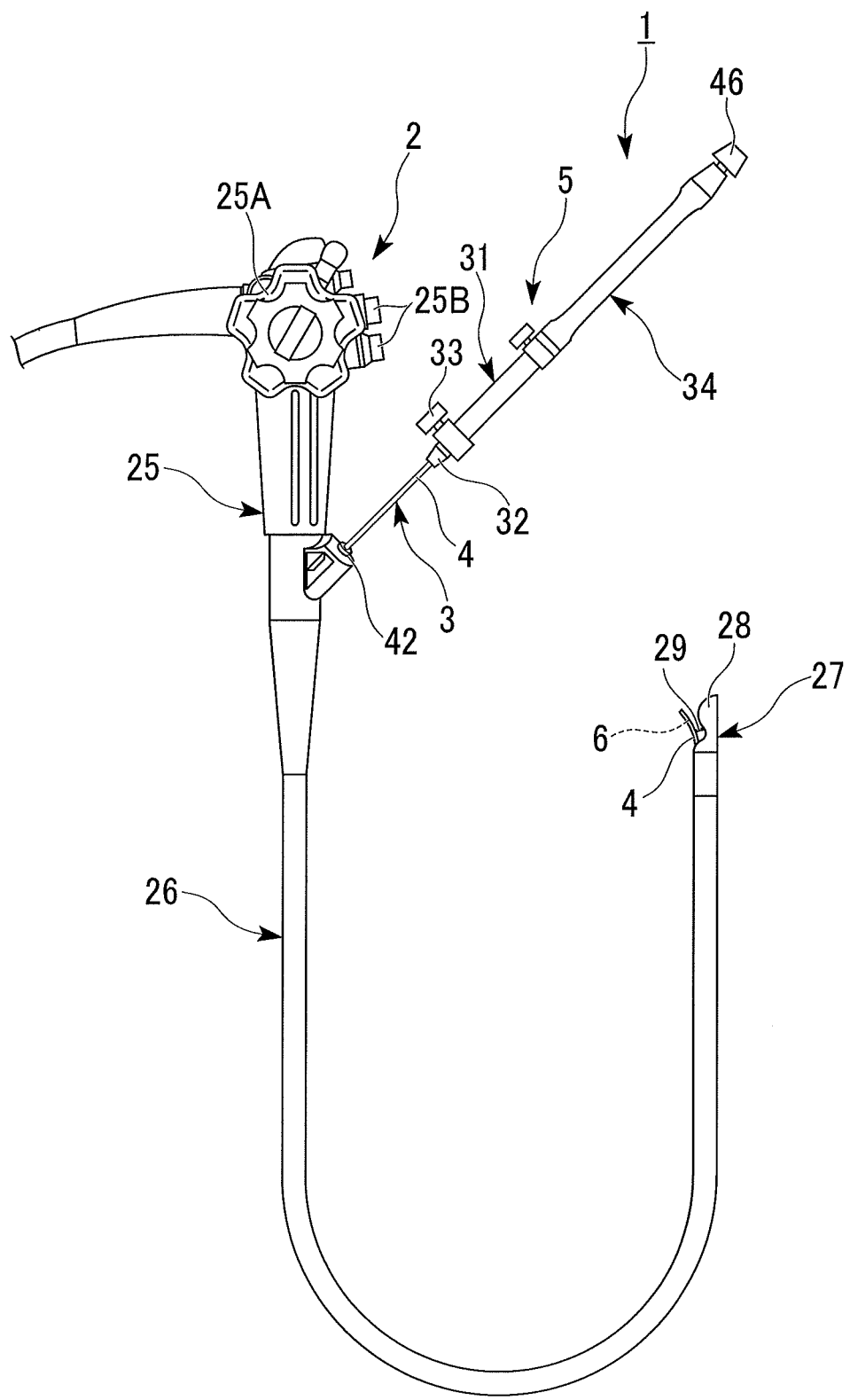
FIG. 1 shows the usage status of applicator inserted in an endoscope.

As shown in FIG. 1, the applicator, which is a flexible treatment instrument, is provided with an insertion portion 3 that passes through an instrument channel of an endoscope 2. The insertion portion 3 has a flexible hollow sheath 4 longer than the instrument channel. The base end of the sheath 4 placed outside the body has an operation part 5 fitted thereto. A surgical portion 6 is disposed at the front end of the sheath 4 drawn out from the front end of the endoscope 2 and led into the body.

Figure 2:
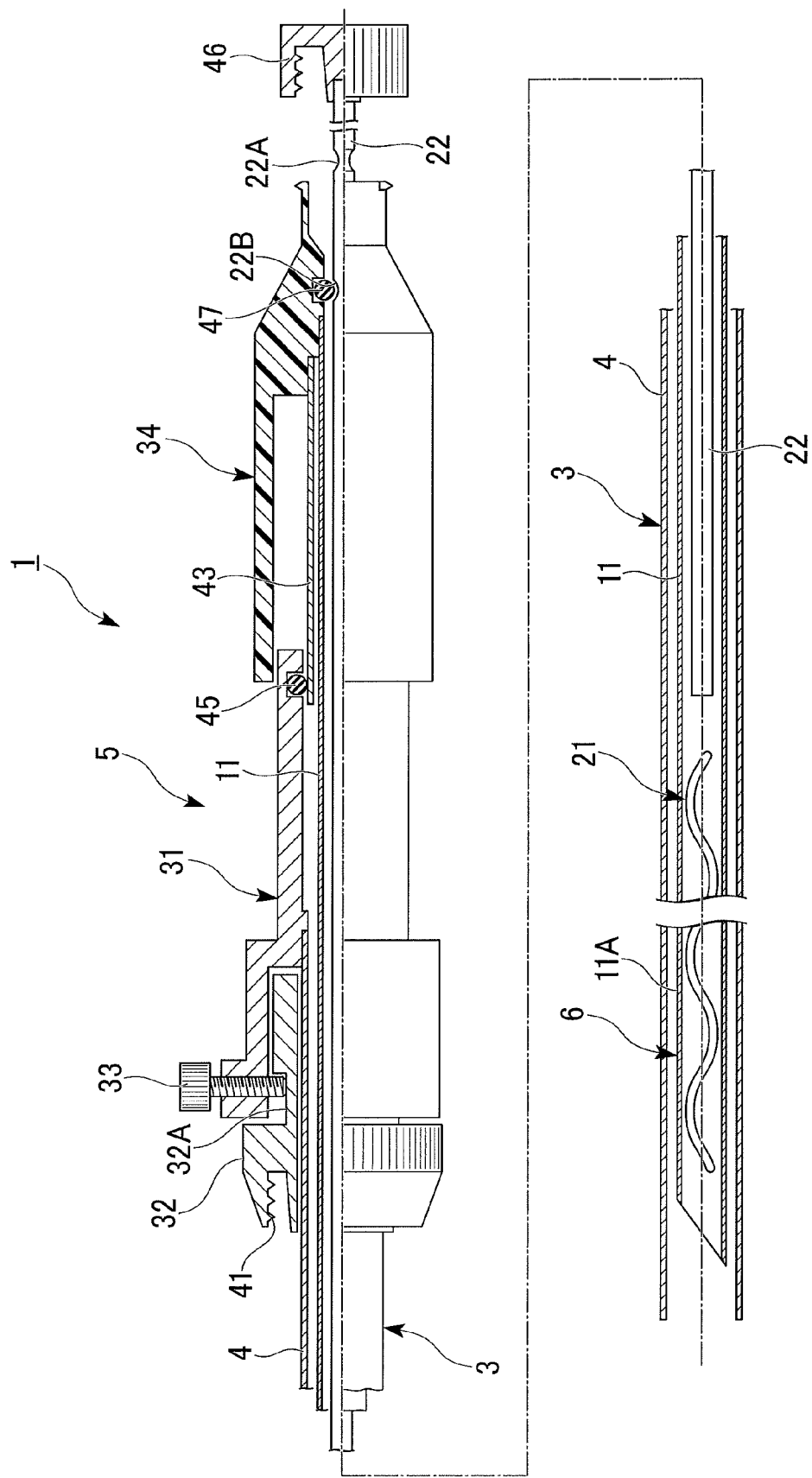
FIG. 2 is a cross sectional view showing the applicator configuration.

As shown in FIG. 2, the surgical portion 6 is formed from a deployed section 11A at the front end of a needle tube 11 that can be freely advanced/retraced through the sheath 4. The needle tube 11 is hollow, passes through sheath 4 and connects with the operation part 5. The needle tube 11 cannot be expanded/contracted, but it has the flexibility to bend to a certain extent when it is inserted into the body. The needle tube 11 has only a deployed section 11A at the front end; only the deployed section 11A may be free to protrude in the sheath 4. If the operation tube 5 is connected to the deployed section 11A made of material with higher flexibility than the needle tube 11, the insertability can be enhanced further.

Figure 3:
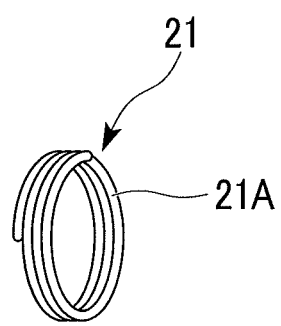
FIG. 3 is an external view of the tissue fastening tool.

The front end of the deployed section 11A is cut incisively, and an opening is formed at the front end. A tissue fastening tool 21 is housed within the deployed section 11A. The tissue fastening tool 21 is inserted after substantially stretching the element wire 21A. As shown in FIG. 3, the tissue fastening tool 21 has a coil shape when it is in the no-load condition. If it is taken out of the deployed section 11A, it returns to its original coil shape by its self-restoring force. In this tissue fastening tool 21, a tightly wound coil spring made of a superelastic alloy such as NiTi may be used. The superelastic alloy exhibits superelasticity when a specific temperature is exceeded; it maintains its properties of shape memory in environments below a specific temperature. Accordingly, if the coil spring is extended in temperature environments at which shape memory characteristics are active, the extended state can be retained. If inserted in the deployed section 11A in this state, assembly can be easily performed. The method of insertion in the deployed section 11A is not limited only to the method mentioned above. Moreover, the tight winding is not limited to the coil spring only.

As shown in FIG. 2, a stylet 22 is inserted in the deployed section 11A in addition to the tissue fastening tool 21. The stylet 22 is inserted to the base end side relative to the tissue fastening tool 21 such that it can be freely advanced/retracted. It is a pusher that pushes the tissue fastening tool 21 from the deployed section 11A by operating the operation part 5 through the needle tube 11.

The operation part 5 has a hollow operation part body 31 to which the sheath 4 is fixed. A connector 32 is inserted on the side of the front end in the operation part body 31, and is fixed by the securing screw 33. A slider 34 is fitted on the base end side of the operation part body 31 such that it can be advanced/retracted freely.

Internal thread 41 is formed in the connector 32, and it can be connected to the connector 42 (refer to FIG. 1) of the instrument channel of the endoscope 2. One annular groove 32A is formed in the part of the connector 32 inserted in the operation part body 31. If the tip of the securing screw 33 is tightened when fitted in the groove 32A, the operation part body 31 and the connector 32 become fixed, and they can no longer rotate or advance/retract in the axial direction. If the securing screw 33 is loosened slightly, the connector 32 can be rotated along the groove 32A. If the securing screw 33 is loosened further and taken off from the groove 32A, the connector 32 can be rotated and advanced/retracted.

The slider 34 is a member for advancing/retracting the needle tube 11; it is fitted such that it can move only in the advancing/retracting direction in the operation part body 31. A protective tube 43 and the needle tube 11 are fixed on the inside of the slider. The protective tube 43 is fixed more to the outside than the needle tube 11; it prevents deflection of the needle tube 11. Furthermore, the protective tube 43 is attached to the O-ring 45 supported on the side of the operation part body 31 by a friction fit. It offers the feel of the operation by generating resistance when the slider 34 is advanced/retracted, and also prevents the backflow of air or mucus from the body. The O-ring 45 is made of a flexible material such as silicone rubber.

The stylet 22 that passes through the needle tube 11 is pulled out penetrating through the slider 34. A stylet knob 46 is fitted at its end. A first groove 22A and a second groove 22B are carved onto the stylet 22 at specific spacing in the advancing/retracting direction. These grooves 22A, 22B give a 'click' feeling when they form a friction fit with the O-ring 47 supported on the side of the slider 34. The second groove 22B is installed to correspond to the position at which the tissue fastening tool 21 starts to get pushed out; it has the role of preventing the tissue fastening tool 21 from being needlessly pushed out and of enhancing operability. The first groove 22A is placed between the start of the push-out and the completion of push-out of the tissue fastening tool 21. For example, it may be at a position corresponding to the position at which the tissue fastening tool 21 is pushed out halfway. The first groove 22A gives a "click" feeling to the advance/retraction of the stylet 22, and also has the role of controlling the push-out amount of the tissue fastening tool 21. Although only one first groove 22A is illustrated, the position of the first groove 22A may be shifted and two grooves may be provided. The O-ring 47 prevents the backflow of air or mucus from the body, and is made of a soft material such as silicone rubber.

The stylet 22 is provided with flexibility that enables it to be inserted in the instrument channel of the flexible endoscope 2, but if the flexibility of the exposed part outside the slider 34 at the front side is reduced, operability can be improved.

FIG. 1 shows the linear scanning type ultrasonic endoscope as the endoscope 2 used together with the applicator 1. The endoscope 2 is provided with a flexible insertion portion 26 that extends from the operation part 25 used outside the body. A knob 25A for bending the front end part of the insertion portion 26 into a curve and various buttons 25B are provided in the operation part 25. A cover 27 is fitted at the front end of the insertion portion 26. An ultrasonic probe 28 is fitted to the cover 27. The ultrasonic probe 28 is placed on the flat plane passed through the axial line of the insertion portion 26. A plurality of ultrasonic transducers are disposed along the periphery of the circular arc shape. Furthermore, the endoscope 2 is provided with a forceps elevator 29 for delivery of the front end of the applicator 1 in the lateral direction, and the direction of delivery of the applicator 1 can be adjusted at a portion located proximally to the operator. The endoscope 2 may be provided with ultrasonic probe of other types. Moreover, an endoscope not provided with the ultrasonic probe 28 may also be used. In this case, an ultrasonic probe used outside the body, an X-ray device, a magnetic resonance imaging (MRI) device, or a computerizing tomography (CT) device may be used jointly.

Figure 4:
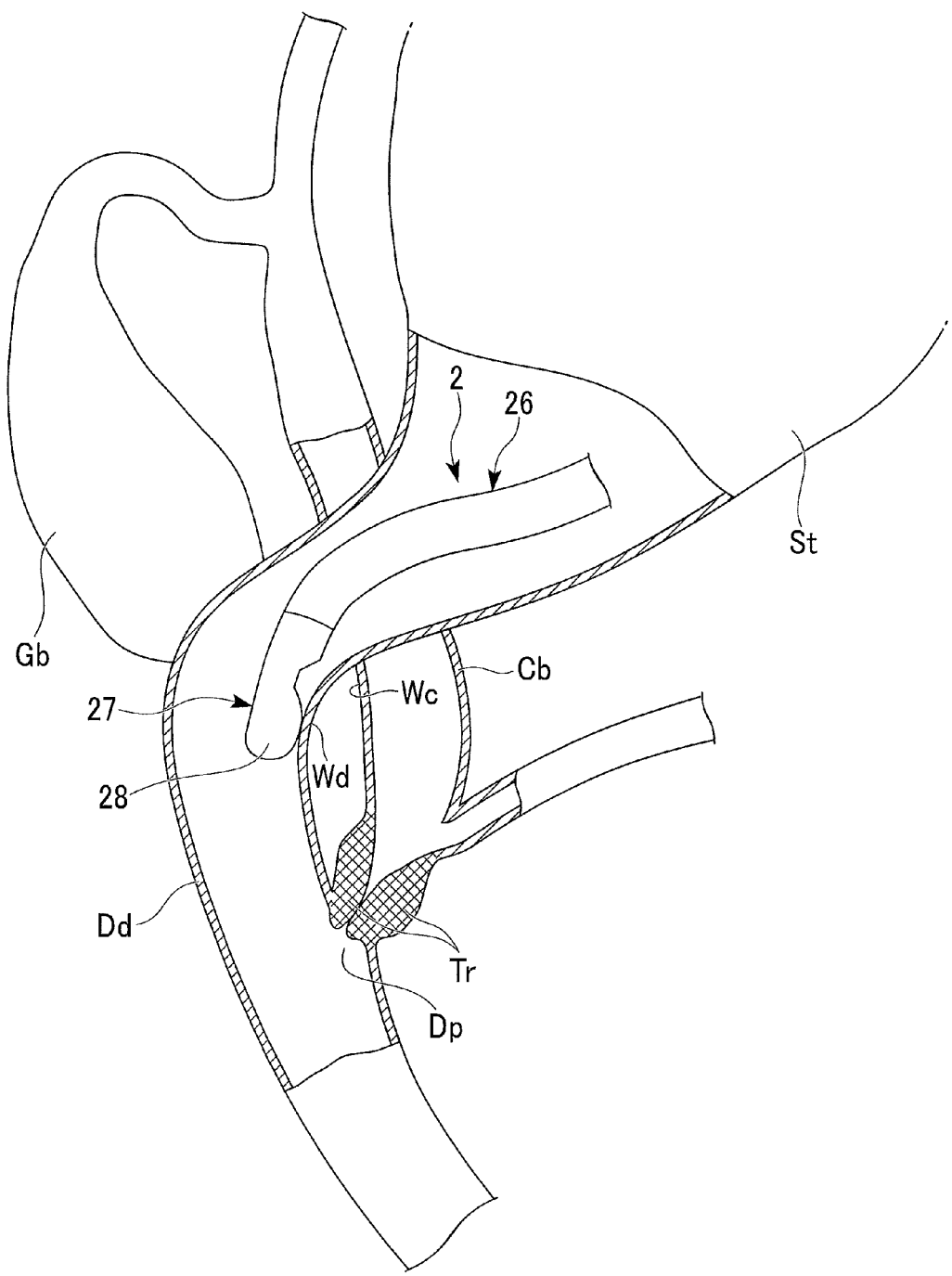
FIG. 4 shows an endoscope inserted in the duodenum.

Next, the procedure to make bypass between common bile duct and duodenum after joining them is described here. As shown in FIG. 4, this kind of procedure is performed when the duodenal papilla Dp is obstructed by a tumor Tr preventing bile drainage, consequently the bile assimilates in the blood and causes jaundice. This procedure enables the direct drainage of bile from the common bile duct Cb to the duodenum Dd.

First, the endoscope 2 is inserted from the patient's mouth. The endoscope 2 is inserted in the duodenum Dd, which is the upper alimentary tract. The condition outside the duodenum Dd is examined by the ultrasonic probe 28, and an appropriate location proximally to the common bile duct Cb for the procedure is searched around the stomach St side in relation to the duodenal papilla Dp.

Figure 5:
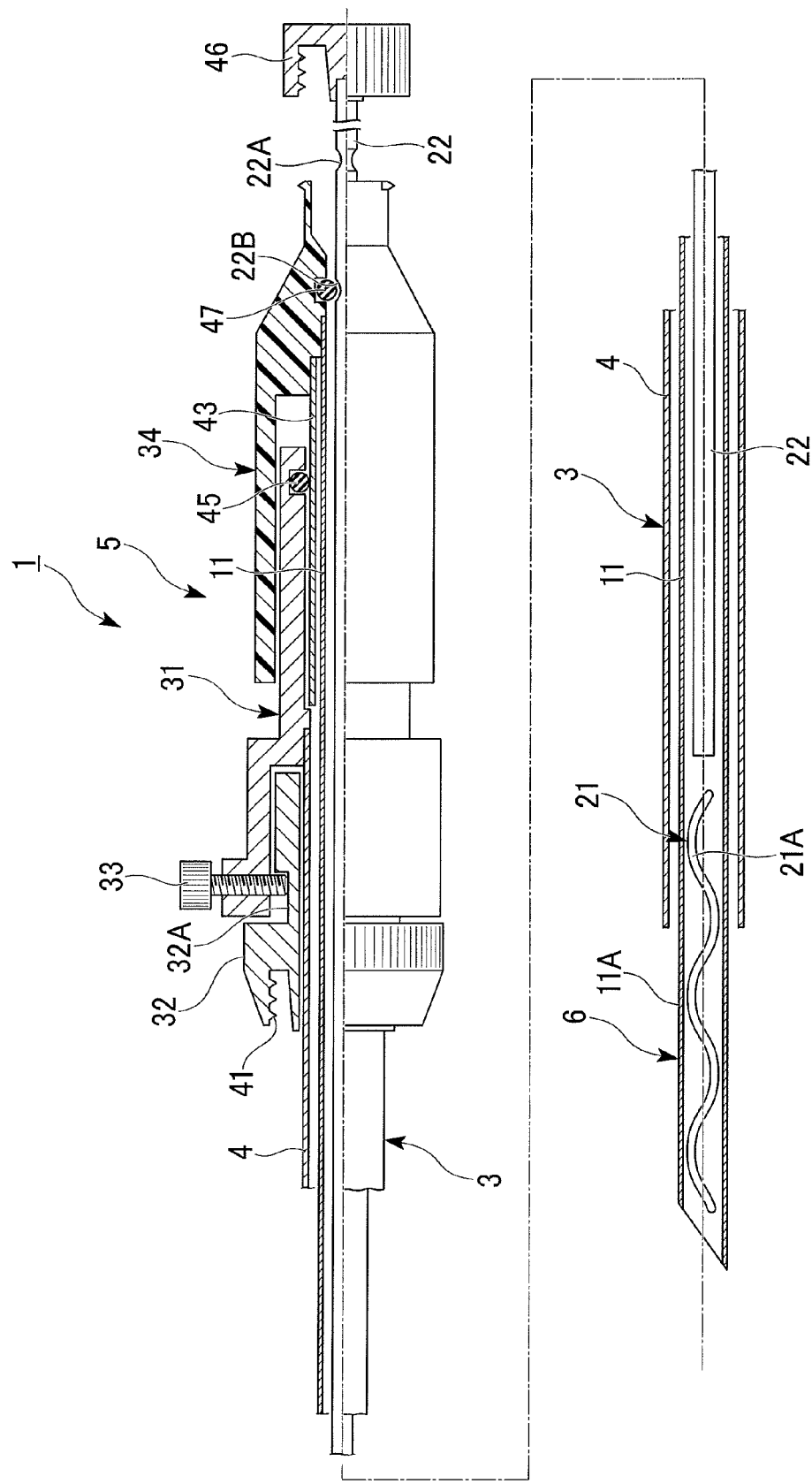
FIG. 5 is a cross sectional view showing the deployed section protruding from the front end of the applicator.

The applicator 1 is advanced through the instrument channel, and the protruding direction is adjusted with the forceps elevator 29. As shown in FIG. 5, the slider 34 of the operation part 5 is pushed into the operation part body 31. The needle tube 11 fixed in the slider 34 advances, and the deployed section 11A protrudes from the front end of the sheath 4. Since the second groove 22B is joined to the slider 34 through the O-ring 47, the stylet 22 advances together with the needle tube 11.

Figure 6:
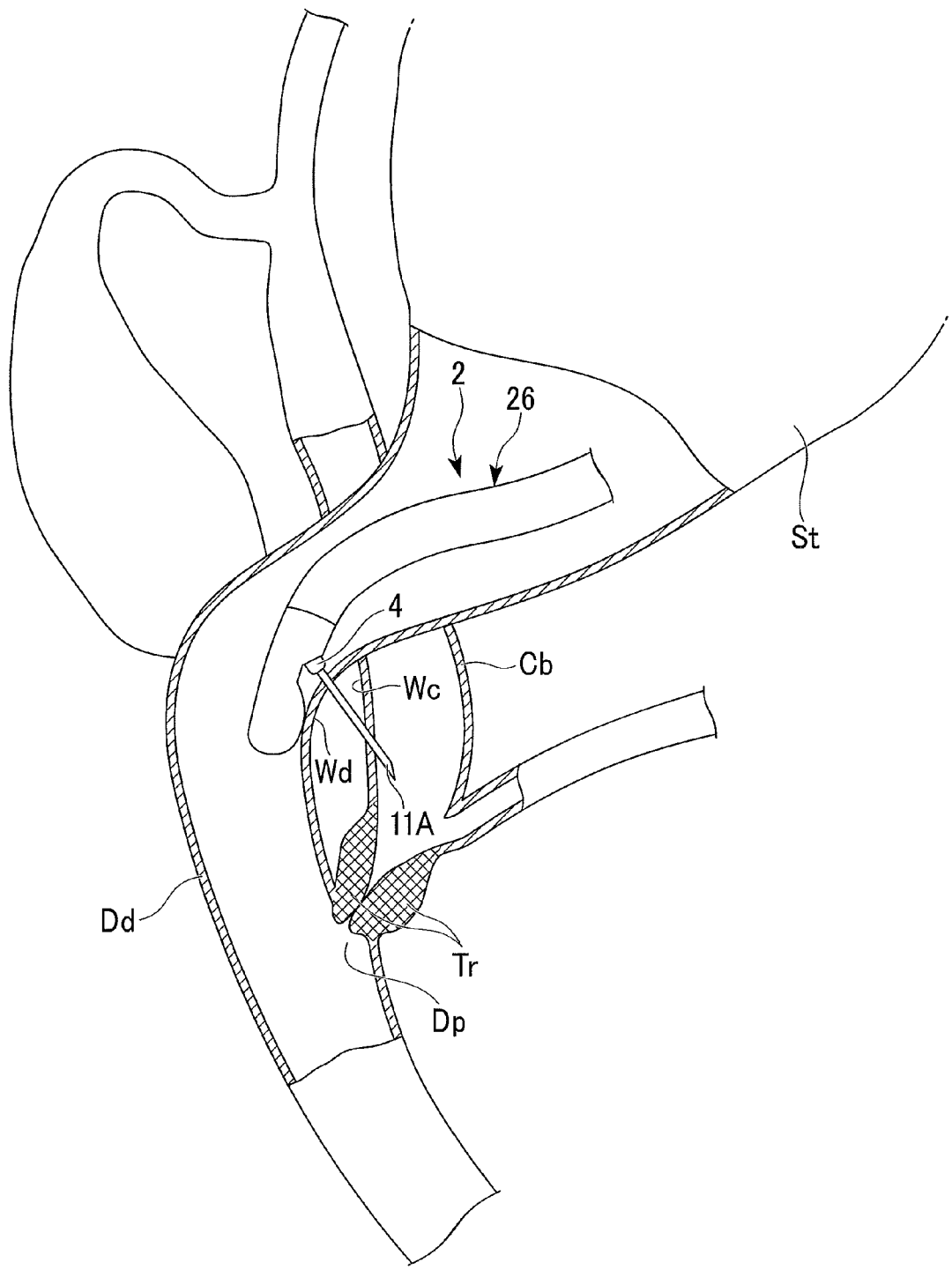
FIG. 6 shows the penetrated deployed section extending from the duodenum toward the common bile duct.

As a result, the deployed section 11A passes completely through from the inside to the outside of the duodenum wall Wd, as shown in FIG. 6, and furthermore, passes through the outside to the inside of the common bile duct wall Wc.

Figure 7:
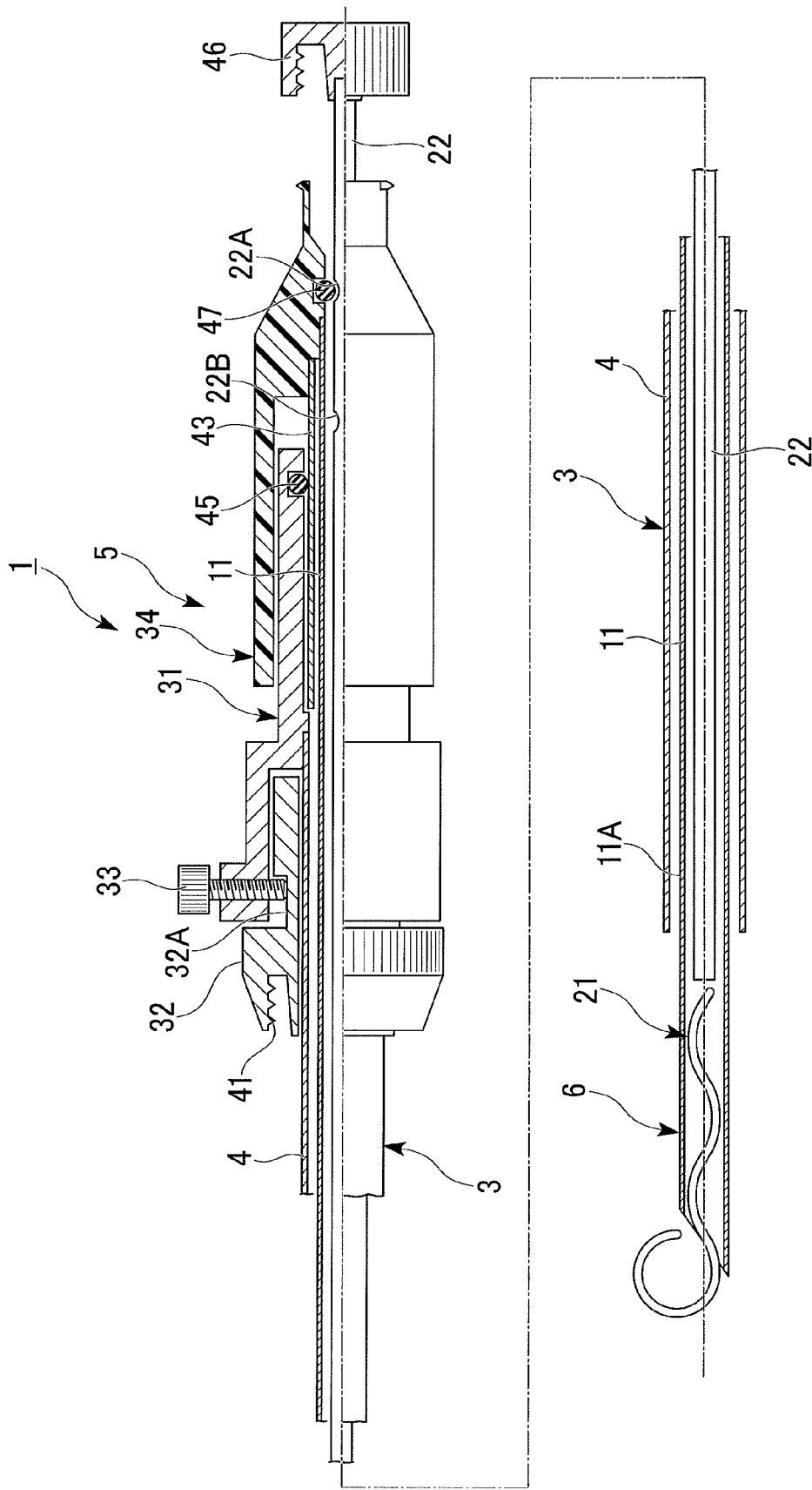
FIG. 7 shows the view when the stylet has been advanced to push out the tissue fastening tool halfway.
Figure 8:
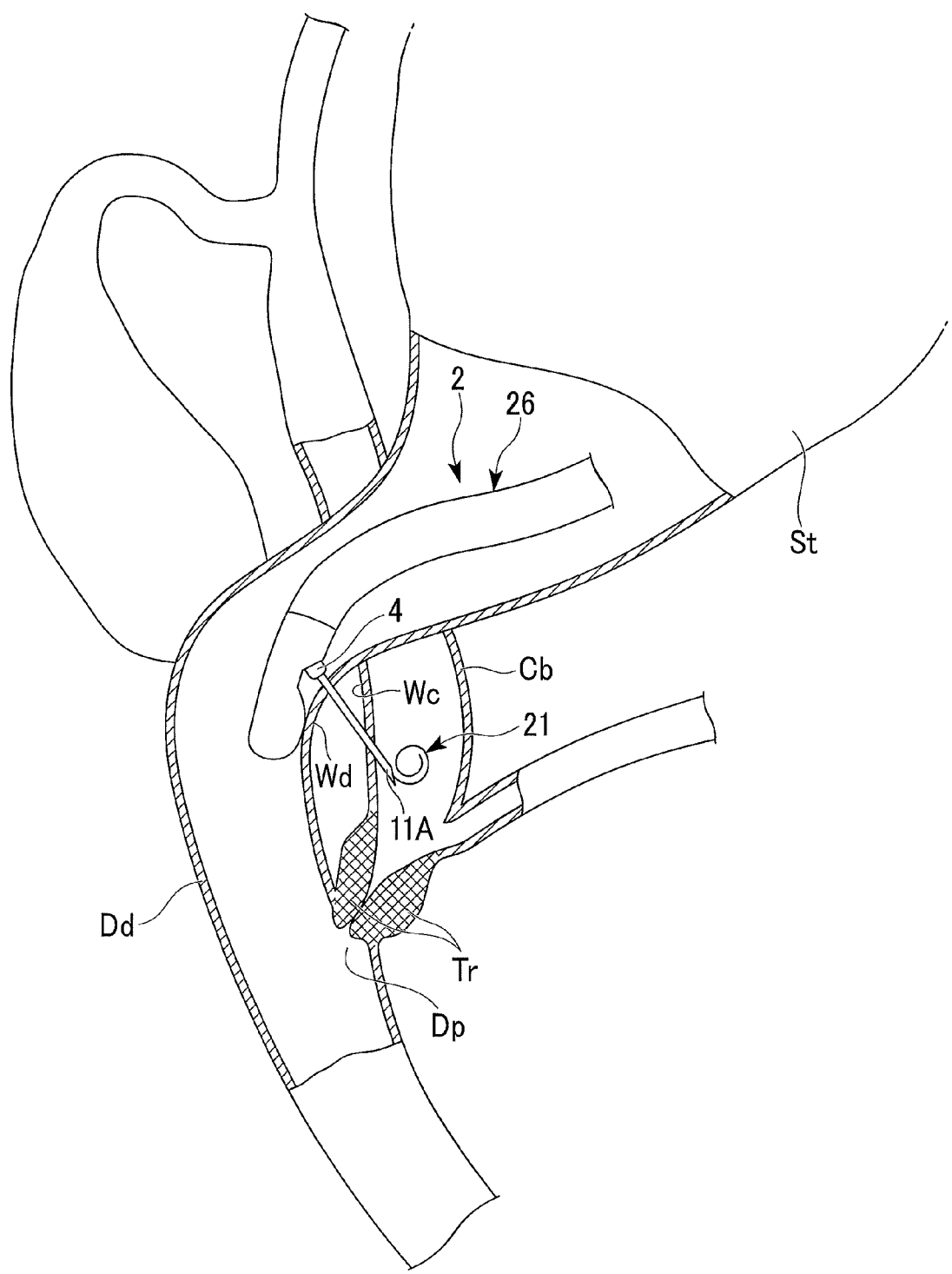
FIG. 8 shows the disposition of the tissue fastening tool when it has been pushed out halfway.

As shown in FIG. 7, a first groove 22A is joined by friction with the O-ring 47 by pushing the stylet knob 46. The stylet 22 pushes out the tissue fastening tool 21 into the common bile duct Cb from the front end opening of the deployed section 11A only for a length substantially equal to the distance the stylet knob 46 has moved. The push-out distance at this stage should preferably be a length equivalent to substantially half the total length of the tissue fastening tool 21. As shown in FIG. 7 and FIG. 8, a part of the tissue fastening tool 21 pushed into the common bile duct Cb restores itself into coil shape because of superelasticity.

Figure 9:
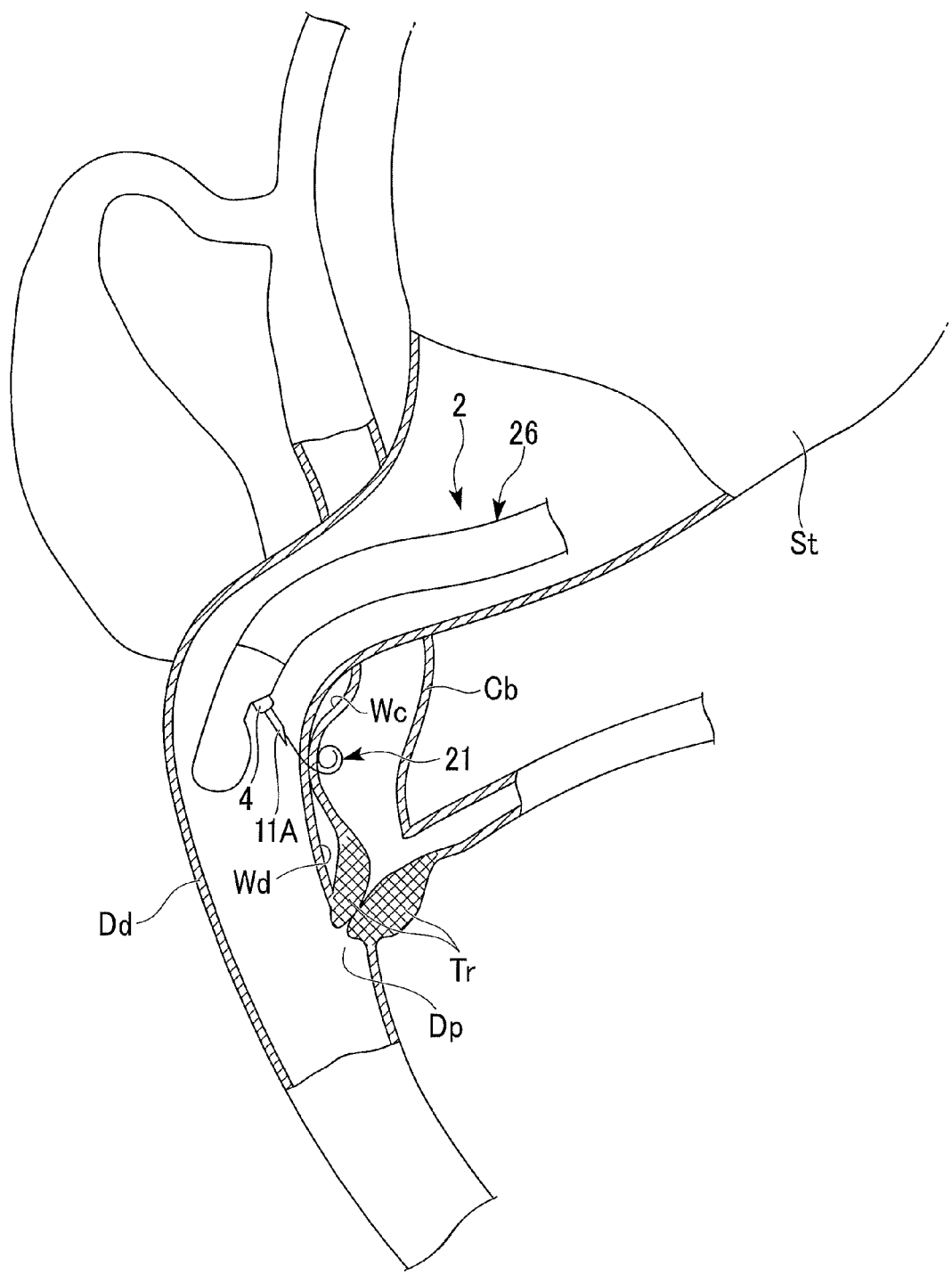
FIG. 9 shows the common bile duct pulled up in the duodenum with the deployed section pulled back from the condition in FIG. 8.

Thereafter, the applicator 1 is retracted, the deployed section 11A is pulled out of the common bile duct Cb, and is pulled back into the duodenum Dd. As shown in FIG. 9, the tissue fastening tool 21 restored to its original coil shape, forms a closed space and comes into annular contact with the inner wall of the common bile duct Cb. This part becomes the anchor, and the common bile duct Cb is pulled toward the duodenum Dd so as to form an anastomosis.

Figure 10:
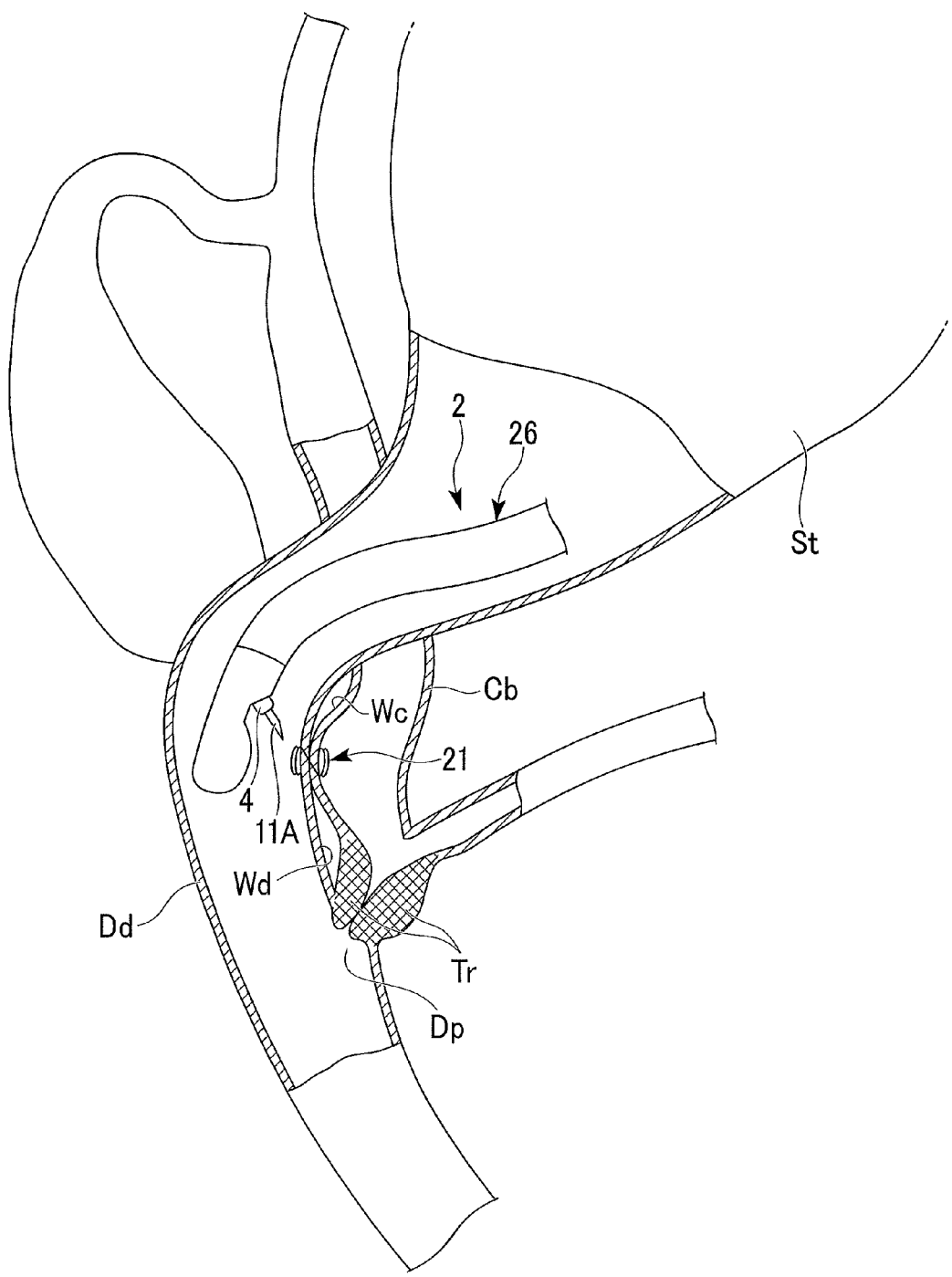
FIG. 10 shows the fully pushed out tissue fastening tool.
Figure 11:
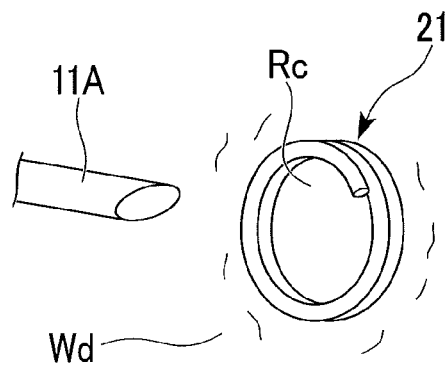
FIG. 11 is the external view of the tissue fastening tool detained in the tissue.

The stylet knob 46 is advanced further, and the remaining part of the tissue fastening tool 21 is pushed out from the deployed section 11A by the stylet 22. As shown in FIG. 10, the tissue fastening tool 21 is completely released from the applicator 1, and the part on the side of the duodenum Dd is also restored to its original coil shape because of the superelasticity. As a result, the duodenum wall Wd and the common bile duct wall Wc are fastened by the tissue fastening tool 21 in a close contact condition. As shown in FIG. 10 and FIG. 11, the tissue fastening tool 21 is detained in coil shape on both the duodenum Dd side and the common bile duct Cb side, that is, when viewed from the axial direction of the coil, the tissue fastening tool 21 is detained in an annular contact condition with the tissue.

Figure 12:
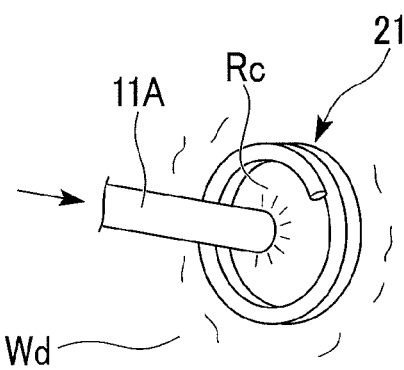
FIG. 12 shows the closed area formed by the tissue fastening tool pierced by the deployed section.
Figure 13:
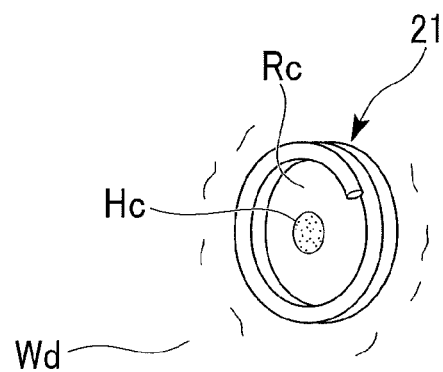
FIG. 13 shows the anastomosis hole formed by the deployed section.
Figure 14:
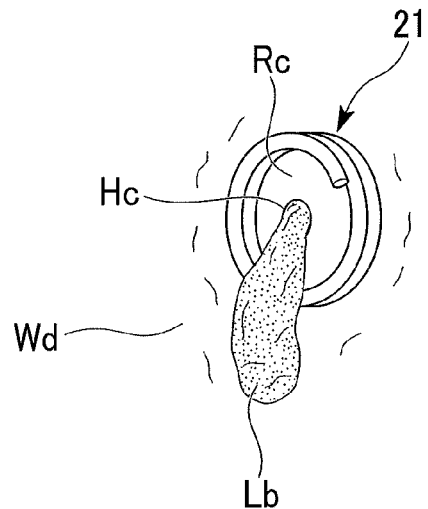
FIG. 14 shows a schematic drawing of the status of bile draining into the duodenum from the anastomosis hole.

At this stage, the closed area is formed between the duodenum wall Wd and the common bile duct wall Wc by the tissue fastening tool 21; therefore, the deployed section 11A is again advanced, and passed completely through the tissue of the closed area Rc formed by the tissue fastening tool from the duodenum wall Wd to the inside of the common bile duct wall Wc, as shown in FIG. 12. At this stage, the stylet 22 is slightly pulled back beforehand, and the incisive front end of the deployed section 11A is used to pierce the area Rc. When the deployed section 11A is pulled out, as shown in FIG. 13, the anastomosis hole Hc is formed in the closed area Rc fastened by the tissue fastening tool 21. As shown in FIG. 14, the bile Lb drains from the common bile duct Cb to the duodenum Dd through the anastomosis hole Hc, and jaundice is treated.

Figure 15:
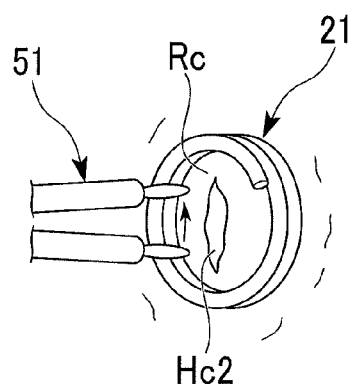
FIG. 15 is an explanatory drawing showing the formation of the anastomosis hole using a high-frequency knife.

The area of the anastomosis hole Hc can be adjusted by puncturing the deployed section 11A several times, or by moving the deployed section 11A in the punctured state. Also, as shown in FIG. 15, a large fistulous opening Hc2 may be formed by incising with the high-frequency knife 51. The high-frequency knife 51 may be inserted instead of the applicator 1 or approached through a separate instrument channel.

According to the present embodiment, the duodenum Dd and the common bile duct Cd can be joined by procedure through a natural orifice. Moreover, a bypass procedure for linking both organs can be performed. By selecting the duodenum Dd as the first hollow organ and the common bile duct Cb as the second hollow organ, the drainage path of the bile can be ensured when the duodenal papilla Dp is obstructed. In the conventional procedure through a natural orifice, a stent was inserted in the duodenal papilla Dp, but in cases of advanced obstruction, stent could not be inserted. According to this embodiment, treatment of jaundice can be correctly performed. Compared to transcutaneous procedures, the invasiveness can be reduced. Even locations that are difficult to perform transcutaneously, can be easily treated. In the conventional procedure, open abdominal surgery has been performed to anastomose the common bile duct and the duodenum. However, the physical burden on the patient was heavy; sometimes the bile is leaked out from a slight gap in the sutured section between the common bile duct and the duodenum into the abdominal cavity, causing a serious side effect called bile peritonitis. When an anastomosis is formed between the common bile duct and the duodenum according to the present invention, bile does not leak out into the abdominal cavity from between the common bile duct and the duodenum. Accordingly, there is no concern of bile peritonitis to occur.

Furthermore, long term patency of the bypass is anticipated by this embodiment. In the conventional procedure for inserting stent, a foreign object was detained in the body; therefore, as early as one month, and latest by three months to about six months, the internal hole for the stent becomes obstructed and bile can no longer be drained. Thus, periodic stent replacement was necessary, placing a heavy burden on patients. According to the present embodiment, the bypass hole through which the bile drains does not obstruct easily because it is a luminal tissue.

The first hollow organ in the treatment of jaundice may be in the upper alimentary tract. The upper alimentary tract includes the stomach St in addition to the duodenum Dd. The second hollow organ may be the gall bladder Gb, cystic duct or extrahepatic bile duct.

Figure 16:
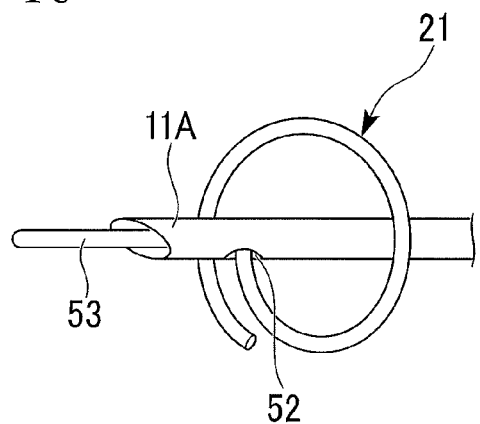
FIG. 16 is an example of modification showing a hole for delivering the tissue fastening tool to the side of the deployed section.

As shown in FIG. 16, an opening 52 may be provided at the side of the deployed section 11A, and the tissue fastening tool 21 may be pushed in from this opening. The coil spring of the tissue fastening tool 21 can be formed laterally with the tissue in the penetrated condition. At this stage, if the guide wire 53 is delivered from the front end opening of the deployed section 11A, two procedures can be performed with one penetration: detention of the tissue fastening tool 21 and the pass-through of the guide wire 53. The second additional procedure is not limited to the pass-through of the guide wire 53 only. Procedures such as injection of a drug solution, a contrast agent, and so on may be performed.

FIG. 17 to FIG. 22 show the other embodiments of the tissue fastening tool.

Figure 17:
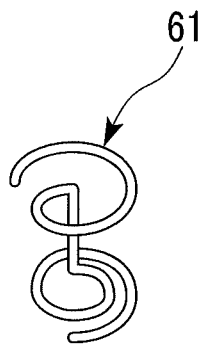
FIG. 17 is an external view showing an example of modification of the tissue fastening tool.

The tissue fastening tool 61 shown in FIG. 17 has both ends of the element wire in convolute form. The part that mainly penetrates the tissue is straight.

Figure 18:
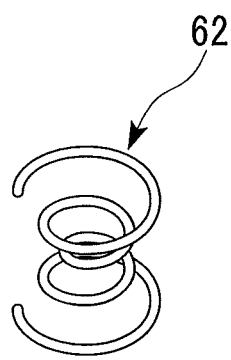
FIG. 18 is an external view showing an example of modification of the tissue fastening tool.

The tissue fastening tool 62 shown in FIG. 18 has a coils of varying winding diameter. The winding diameter is the smallest at the central part in the axial direction and the diameter gradually increases as it approaches either end.

Figure 19:
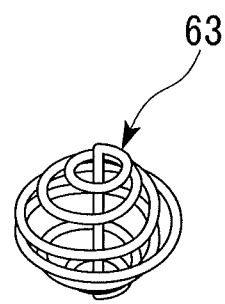
FIG. 19 is an external view showing an example of modification of the tissue fastening tool.

The tissue fastening tool 63 shown in FIG. 19 has a part that extends in a straight line in the axial direction. From both ends of this part, a spiral shape loops back toward the central part. The loop-back part has a winding diameter that gradually increases as it approaches the central part.

Figure 20:
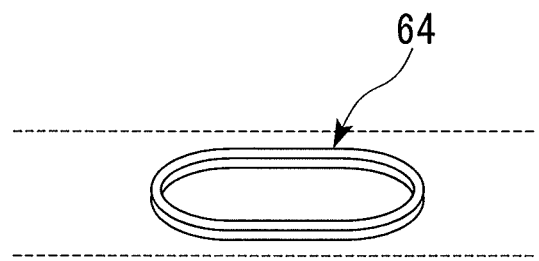
FIG. 20 is an external view showing an example of modification of the tissue fastening tool.

The tissue fastening tool 64 shown in FIG. 20 has an elliptical shape when viewed in the axial direction. If the longer axis of the elliptical shape is aligned in the longitudinal direction of the hollow organ, large puncture area can be ensured even for narrow hollow organs as shown by the broken lines. The shape is not limited to elliptical shape; a shape long on one side such as oblong shape or rectangular shape may also be used. The same effects can be obtained for these shapes also.

Figure 21:
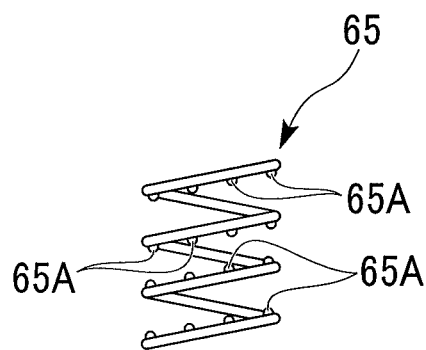
FIG. 21 is an external view showing an example of modification of the tissue fastening tool.
Figure 22:
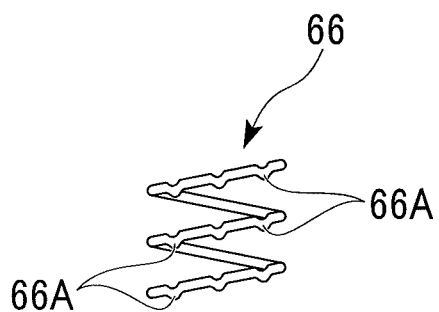
FIG. 22 is an external view showing an example of modification of the tissue fastening tool.

The tissue fastening tool 65 shown in FIG. 21 has non-slip convex parts 65A provided intermittently on the element wire. The convex part 65A is provided in a protruding condition facing the tissue when detained in the body. As shown in the tissue fastening tool 66 in FIG. 22, the convex part 66A may be formed by shaping a part of the element wire in wavy form.

(Second Embodiment)

Figure 23:
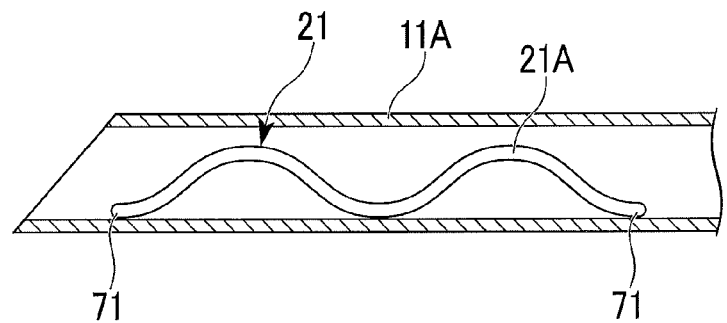
FIG. 23 shows the rounded ends of the tissue fastening tool.

As shown in FIG. 23, the two ends 71 of the element wire 21A in the tissue fastening tool 21 are of rounded shape obtained by chamfering the corners. As shown in FIG. 25, the end 73 may be folded back in a U-shape also. Spherical shapes larger than the element wire diameter may be used, as in the two ends 72 shown in FIG. 24. In this case, the spherical parts may be formed integrally during manufacture, or may be made by caulking and fixing the separate members into this structure. The fixation method used may be brazing, soldering, bonding, or tight fit. When housed in the deployed section 11A or when pushing with the stylet 22, jamming the tissue fastening tool 21 inside the deployed section 11A or the friction between the tissue fastening tool 21 and the deployed section 11A is reduced.

Figure 24:
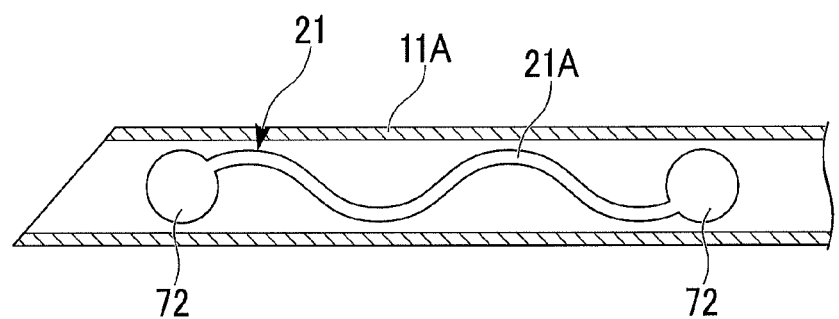
FIG. 24 shows the spherical ends of the tissue fastening tool.
Figure 25:
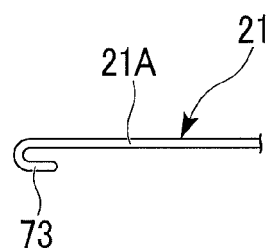
FIG. 25 shows an example of modification of the end of the tissue fastening tool.
Figure 26:
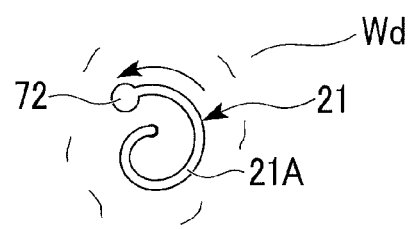
FIG. 26 shows a schematic explanatory drawing of the process of restoring the tissue fastening tool.

According to the embodiment shown in FIG. 24, by making the angle between the inside wall of the deployed section 11A and the element wire 21A as small as possible, the sliding motion can be improved. Furthermore, for example, as shown by the detention state when the end 72 exists as in FIG. 26, when the tissue fastening tool restores its original coil shape in the body, the end 72 of the element wire 21A moves on the surface of the tissue as mentioned above. However, it becomes difficult for the end 72 of the element wire 21A to engage with the tissue, and is thus easy for the original coil shape to be restored. Similar effects can be obtained at the other ends 71, 73.

(Third Embodiment)

Figure 27:
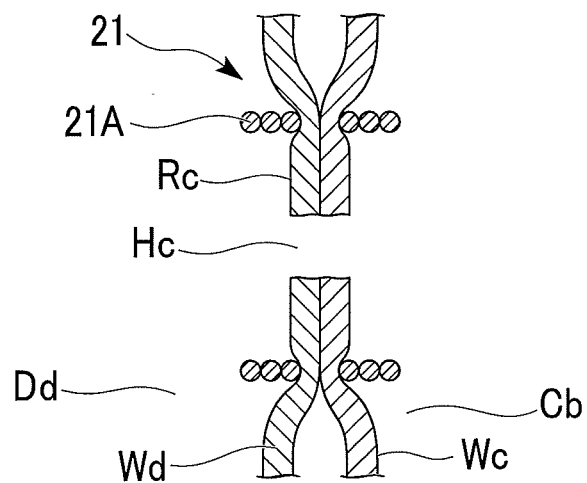
FIG. 27 shows the detention of the tissue fastening tool when its clamping force is large.

FIG. 27 shows the tissue fastening tool 21 detained in the tissue, and the drainage route for bile is ensured. The fastening force of the tissue fastening tool 21 of the present embodiment is strong; the duodenum wall Wd and the common bile duct wall Wc are compressed by the element wire 21A, the tissue inside the area Rc fastened by the tissue fastening tool 21 becomes ischemic condition due to poor blood circulation into the area Rc.

Figure 28:
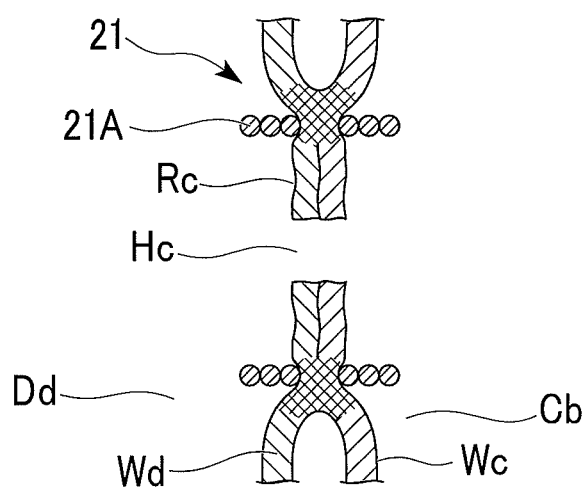
FIG. 28 shows the necrotized tissue fastened by the tissue fastening tool.
Figure 29:
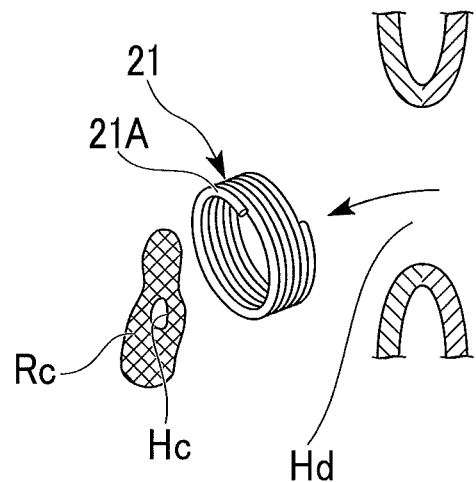
FIG. 29 shows the status of the fistulous opening formed when the tissue fastening tool and the necrotized tissue have fallen into the duodenum side.

As shown in FIG. 28, when the ischemic condition continues, the tissue within the area Rc becomes necrotized. On the other hand, the duodenum wall Wd and the common bile duct wall Wc coalesce and join with each other all around at the outer periphery of the tissue fastening tool 21. When this occurs, the necrotized tissue and the tissue fastening tool 21 fall off, as shown in FIG. 29. The tissue fastening tool 21 is later discharged. After the tissue falls off, a large diameter anastomosis hole (fistulous opening) Hd is formed. At this stage, the portion all around the anastomosis hole Hd connecting the common bile duct Cb and the duodenum Dd has coalesced; therefore, the bile cannot leak out between the common bile duct Cb and the duodenum Dd to the abdominal cavity. Accordingly, there is no concern of bile peritonitis to occur.

According to this embodiment also, similar to the first embodiment, long term patency of the anastomosis hole Hd as the bypass is anticipated. According to this embodiment, since the tissue fastening tool 21 falls off and the bypass hole becomes larger, a longer period of patency than that according to the first embodiment may be anticipated.

The tissue fastening tool 21 is not detained for a long period in the body according to the present embodiment. A fistulous opening Hc of size substantially equal to the size of the tissue fastening tool 21 can be formed.

(Fourth Embodiment)

Figure 30:
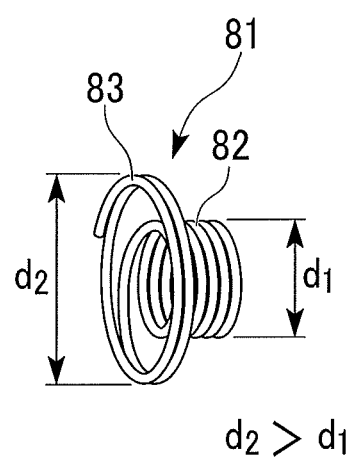
FIG. 30 is a tissue fastening tool with coil shapes of varying winding diameters.

As shown in FIG. 30, the tissue fastening tool 81 is provided with a first part 82 of winding diameter d1 in coil shape, and a second part 83 of winding diameter d2 larger than the first part 82. The material and the method of manufacture of the tissue fastening tool 81 are the same as in the first embodiment.

Figure 31:
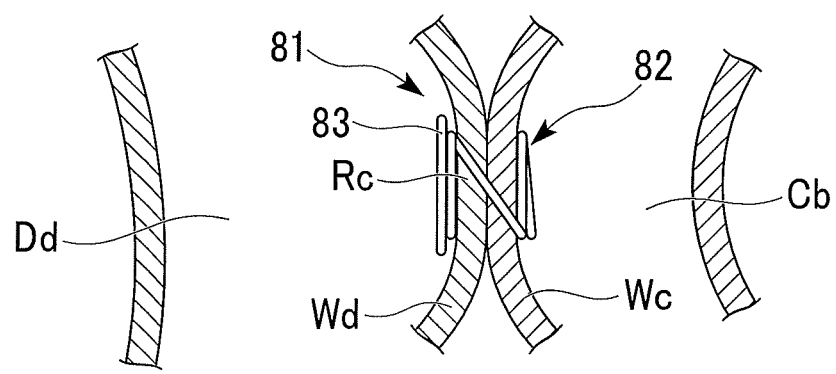
FIG. 31 shows the tissue fastening tool shown in FIG. 30 detained in the tissue.

When housing the tissue fastening tool 81 in the deployed section 11A, the portion corresponding to the second part 83 is inserted first. When fastening the tissue, substantially half the first part 82 is delivered from the deployed section 11A within the common bile duct Cb, and the original coil shape is restored. Subsequently, the deployed section 11A is pulled back into the duodenum Dd, and the remaining substantial half of the first part 82 and the part equivalent to the second part 83 are delivered, and the original coil shape is restored. As shown in FIG. 31, the part 82 with small winding diameter holds and detains the duodenum wall Wd and the common bile duct wall Wc, while the part 83 with the large winding diameter is detained in the duodenum Dd.

Figure 32:
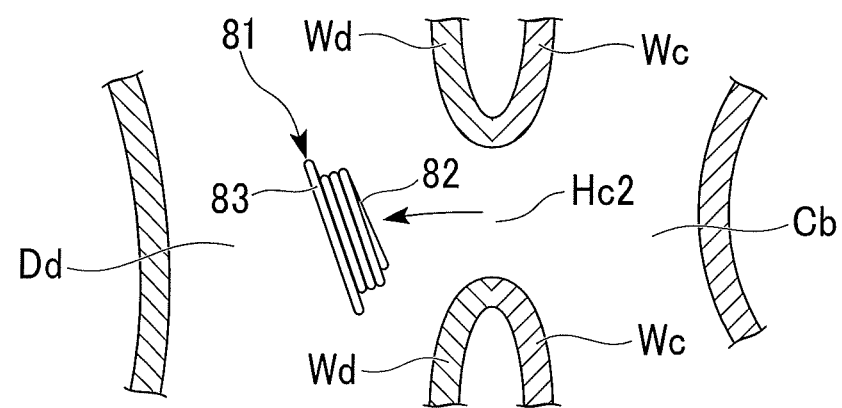
FIG. 32 shows the tissue fastening tool and the necrotized tissue fallen into the duodenum side.

The coil spring is tightly coiled, and the tissue is compressed by the tissue fastening tool 81; therefore, with the passage of time, the tissue is necrotized, and the tissue falls off in the closed area Rc formed by the coil. At this stage, as shown in FIG. 32, the second part 83 with large winding diameter is larger than the first part 82, so the tissue fastening tool 81 and the tissue fall off into the second part 83 side, that is, into the duodenum Dd side. A fistulous opening Hc2 of size substantially equivalent to the winding diameter of the first part 82 is formed between the duodenum Dd and the common bile duct Cb, and from this opening, the bile is drained. Until the tissue is necrotized, the surrounding tissue coalesces; therefore, the common bile duct Cb does not separate from the duodenum Dd. The fallen-off tissue fastening tool 81 is discharged outside the body together with foodstuff.

According to this embodiment, the direction in which the tissue fastening tool 81 falls off is prescribed by varying the winding diameter. If the fall-off direction is set to the duodenum Dd side, then the tissue fastening tool 81 can be correctly discharged out of the body without any additional manipulations.

(Fifth Embodiment)

Figure 33:
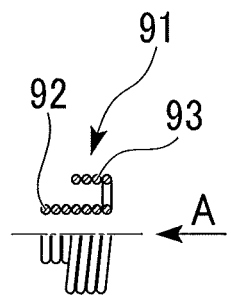
FIG. 33 shows the coil shaped tissue fastening tool partially overlapping in the radial direction.
Figure 34:
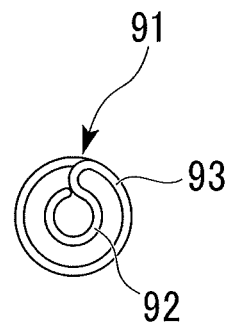
FIG. 34 shows the coil shaped tissue fastening tool partially overlapping in the radial direction as seen from A in FIG. 33.

As shown in FIG. 33 and FIG. 34, the tissue fastening tool 91 is provided with a first part 92 wound in coil shape, and a second part 93 extended to a specific diameter and wound on the outside of the first part 92. The material and the method of manufacturing the tissue fastening tool 91 are the same as in the first embodiment.

Figure 35:
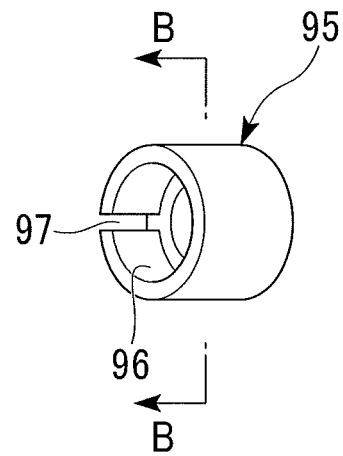
FIG. 35 is an external view of the spacer used when manufacturing the coil of FIG. 33.
Figure 36:
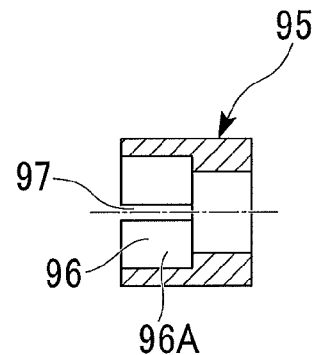
FIG. 36 is a cross sectional view as seen from the line B-B in FIG. 35.
Figure 37:
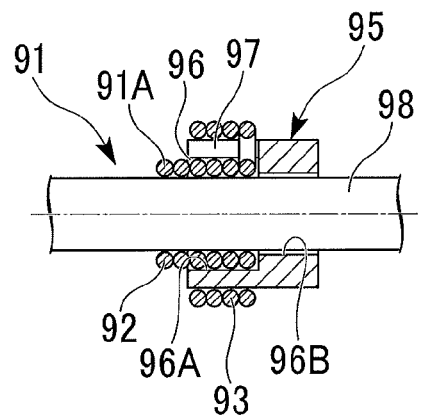
FIG. 37 is an explanatory drawing of the procedure for forming the coil shape of the tissue fastening tool.

When forming the second part 93, a spacer 95 is used as shown in FIG. 35 and FIG. 36. The spacer 95 has a cylindrical shape, and a stepped bore 96 is formed in it. A slit 97 is formed parallel to the axial direction in the part 96A with large diameter of stepped bore 96. During manufacture, as shown in FIG. 37, the element wire 91A, which forms the tissue fastening tool 91, is wound over a core 98 to make the first part 92. Subsequently, it is covered by the spacer 95. In the spacer 95, a small diameter part 96B of bore 96 is passed through the core 98 and the first part 92 is inserted into a large diameter part 96A. The second part 93 is made by pulling out the element wire 91A from the slit 97 and winding it along the outside diameter of the spacer 95. The winding diameter of the second part 93 is decided by the outside diameter of the spacer 95. The two ends of the element wire 91A are fixed so that they do not become loose, and are then shaped by heat treatment.

Figure 38:
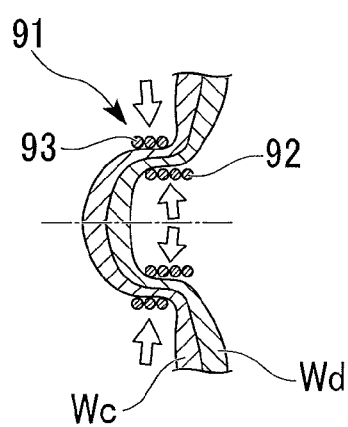
FIG. 38 shows the tissue fastening tool detained in the tissue and fastening forces acting in the radial direction.

When housing the tissue fastening tool 91 in the deployed section 11A, the portion corresponding to the second part 93 is inserted first. When fastening the tissue, the portion corresponding to the first part 92 is delivered from the deployed section 11A within the common bile duct Cb, and the original coil shape is restored. The deployed section 11A is pulled back into the duodenum Dd, the portion corresponding to the second part 93 is delivered and the original coil shape is restored. As shown in FIG. 38, the fastening tool is placed such that the duodenum wall Wd and the common bile duct wall Wc are held between the second part 93 and the first part 92. In addition to the spring force generated when the coil spring is stretched, in the tissue fastening tool 91, a force generated in the radial direction to reduce the diameter also acts on the tissue. The fastening force in the radial direction is generally greater than the spring force in the axial direction, so the tissue can be secured more firmly. If the tissue has been necrotized because of the fastening, the tissue fastening tool 91 and the tissue fall off into the second part 93 side with large diameter. A large diameter opening can be formed and also the tissue fastening tool 91 can be made to fall off with certainty into the duodenum Dd side.

According to the present embodiment, by overlapping a part of the element wire 91A wound in coil shape in the radial direction, the force for fastening the tissue is increased. Also, by forming a large diameter part, the direction in which the tissue fastening tool 91 falls off is specified. If the fall-off direction is set to the duodenum Dd side, then the tissue fastening tool 91 can be discharged out of the body without any additional manipulation.

The tissue fastening tool 91 according to the present embodiment can be made easily by using the method of manufacturing the double coil spring using the spacer 95.

(Sixth Embodiment)

Figure 39:
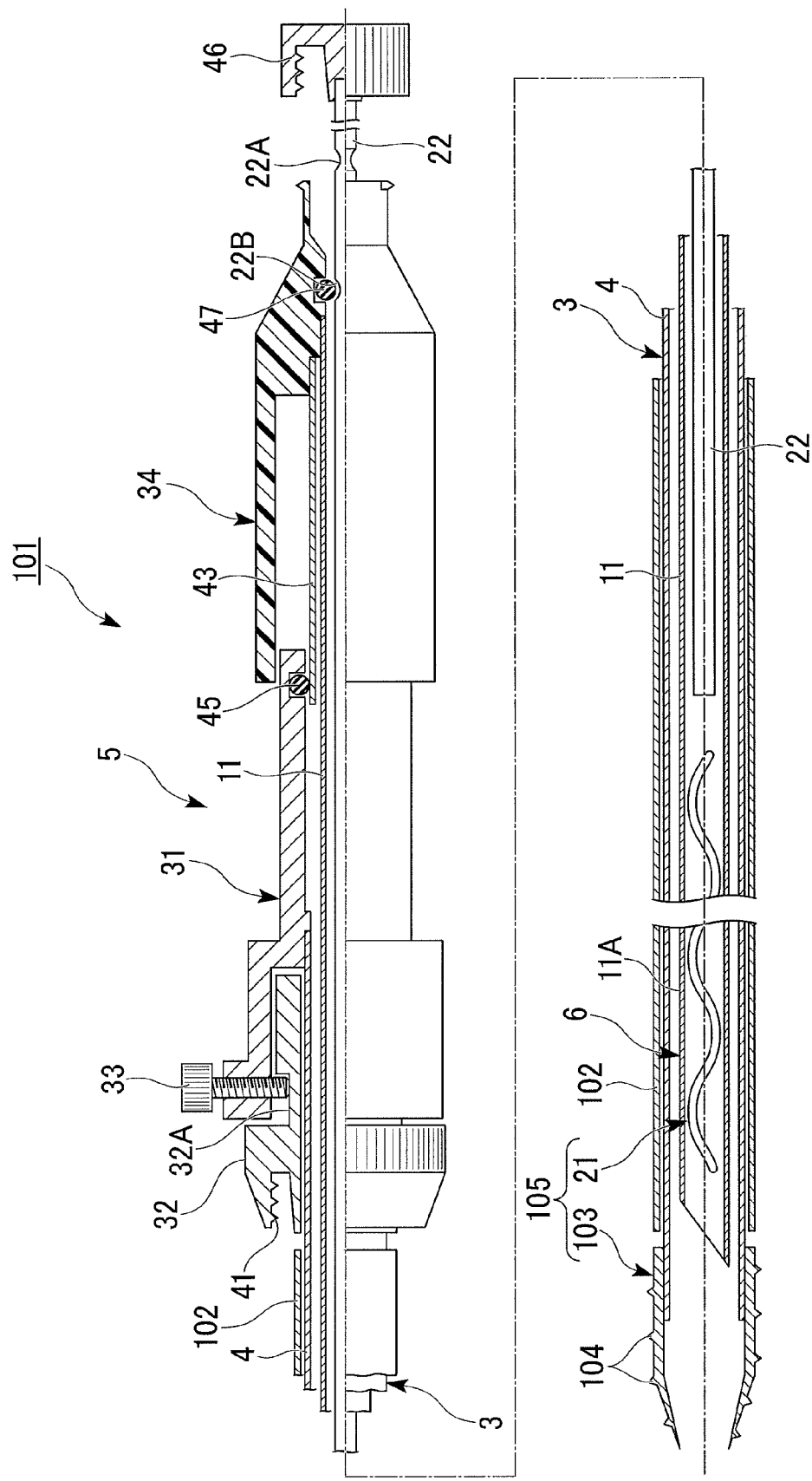
FIG. 39 is a cross sectional view of the applicator when a tissue fastening tool and a stent are used together.

As shown in FIG. 39, the applicator 101 has a double-tube construction with a pusher tube 102 provided on the outside of the sheath 4 that covers the insertion portion 3. A stent 103 is friction fitted at the front end of the sheath 4.

The pusher tube 102 is flexible, and has substantially the same outside diameter as the stent 103. The inside diameter of the pusher tube 102 is slightly larger than the inside diameter of the stent 103, and is not engaged with the stent 103.

The stent 103 has a cylindrical shape, and its front end has a tapered surface enabling it to be smoothly connected to the outside diameter part of the deployed section 11A. Moreover, a thread 104 formed by ridges in spiral shape is provided on the outer periphery.

Figure 40:
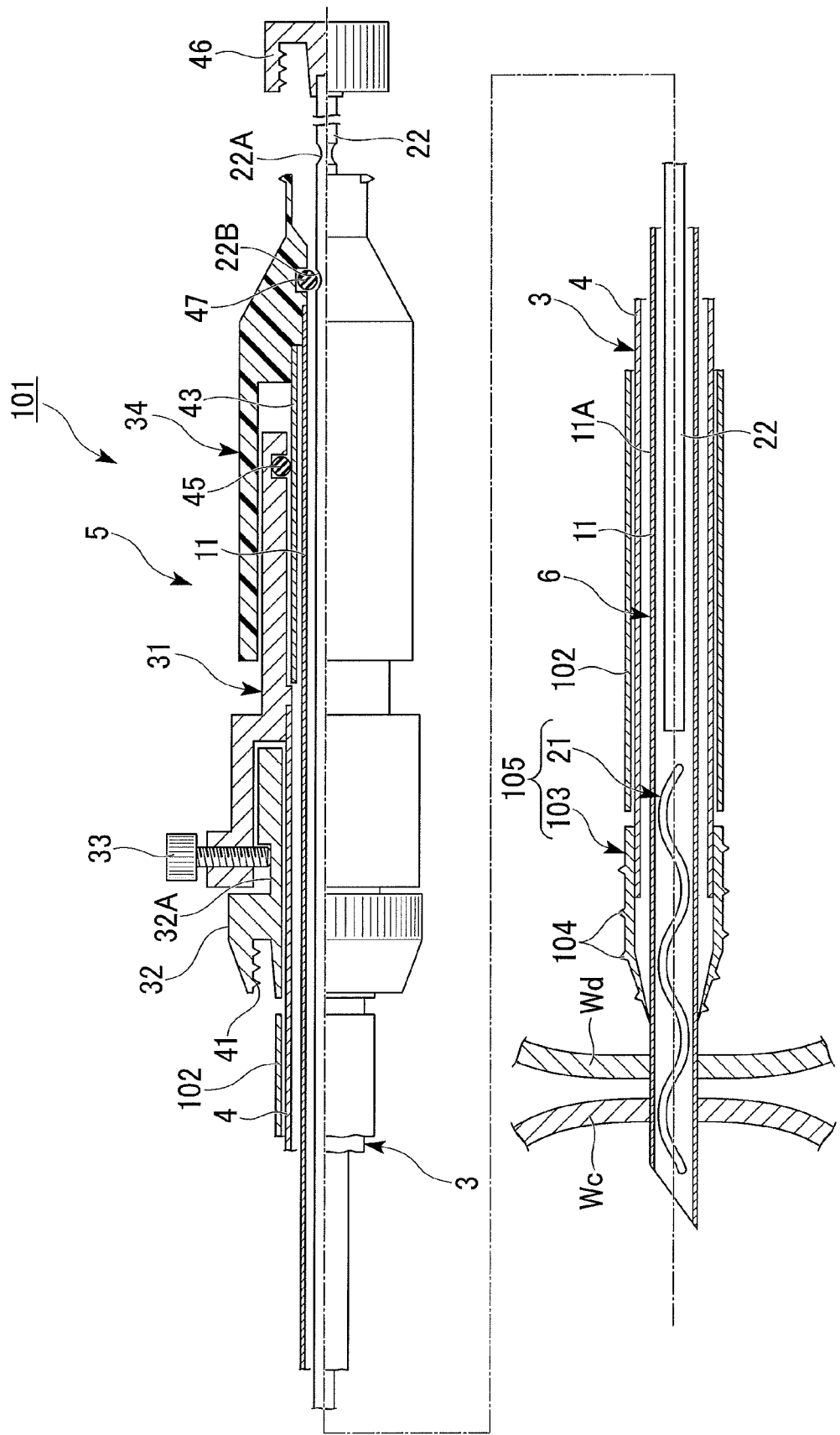
FIG. 40 shows the deployed section protruded by pushing the slider.
Figure 41:
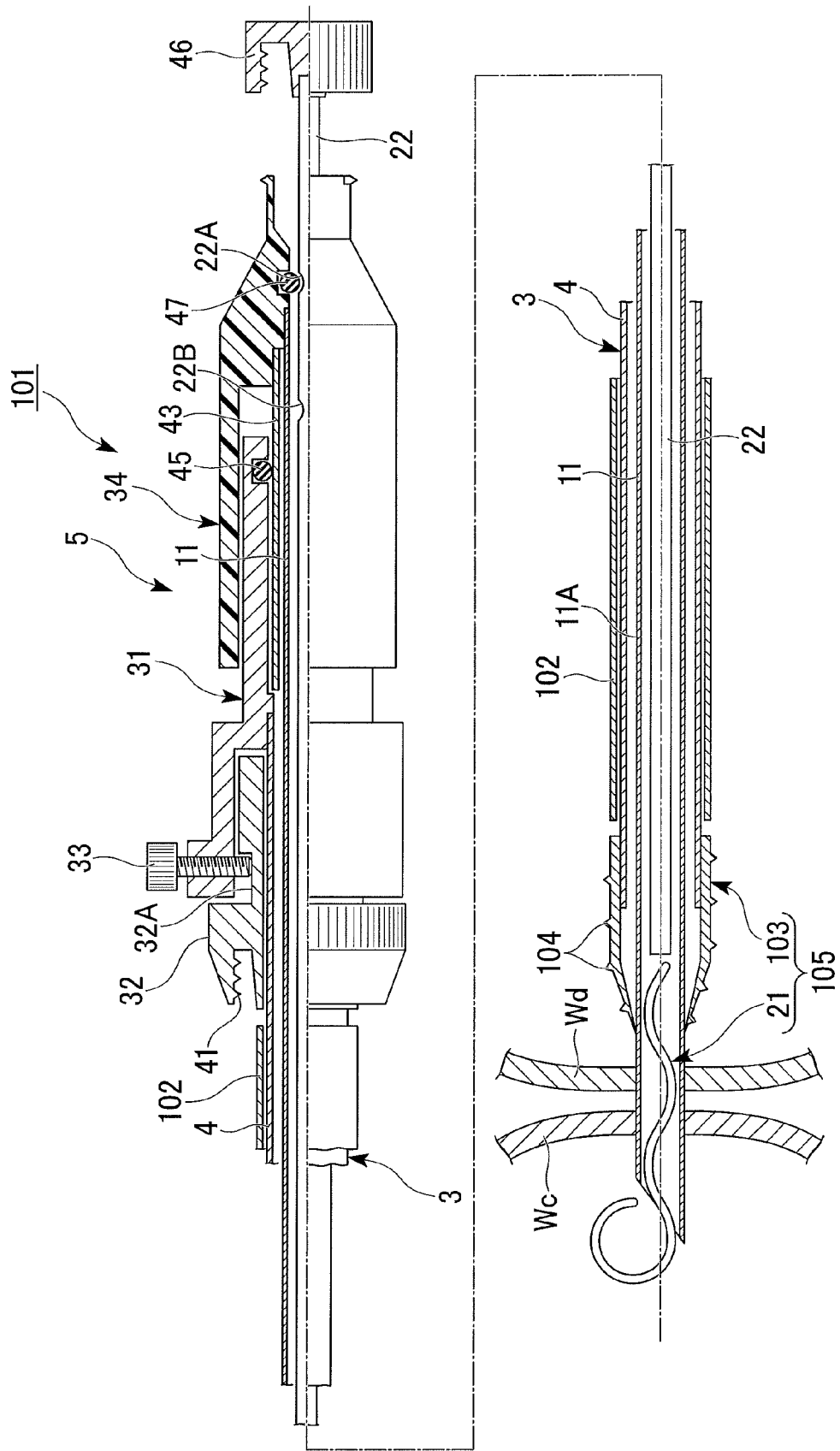
FIG. 41 shows the tissue fastening tool pushed out halfway by pushing the stylet.
Figure 42:
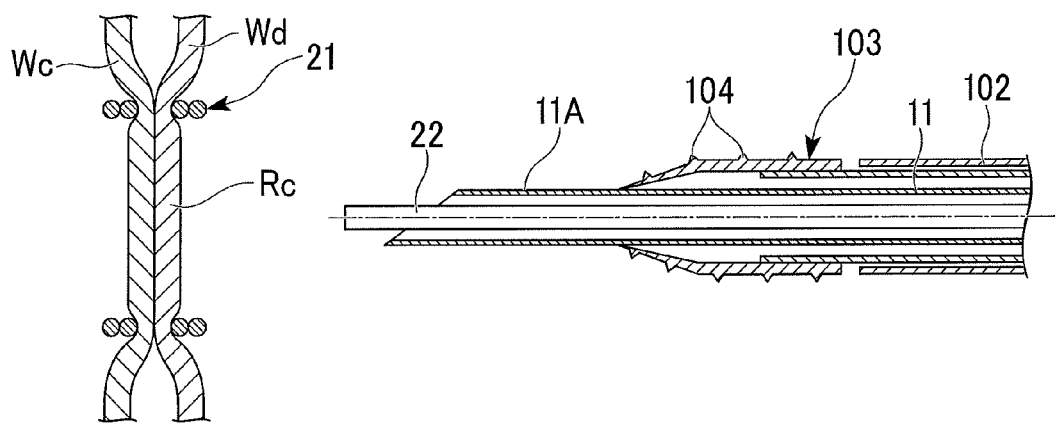
FIG. 42 shows the status of detention of the tissue fastening tool.

When a detention tool 105 made of the tissue fastening tool 21 and stent 103 is detained in the body, as shown in FIG. 40, the deployed section 11A is protruded more to the front end side than the stent 103, and thereafter, the common bile duct wall Wc is pierced from the duodenum wall Wd. In this case, the stent 103 is detained in the duodenum Dd side. As shown in FIG. 41, the stylet 22 is advanced until the first groove 22A engages with the O-ring 47 of the slider 34, and it pushes substantially half of the front end side of the tissue fastening tool 21 in the common bile duct Cb. Next, the deployed section 11A is pulled back to the duodenum Dd side, and the remaining part of the tissue fastening tool 21 is pushed with the stylet 22. As shown in FIG. 42, the tissue fastening tool holds the duodenum wall Wd and the common bile duct wall Wc, restoring its coil shape.

Figure 43:
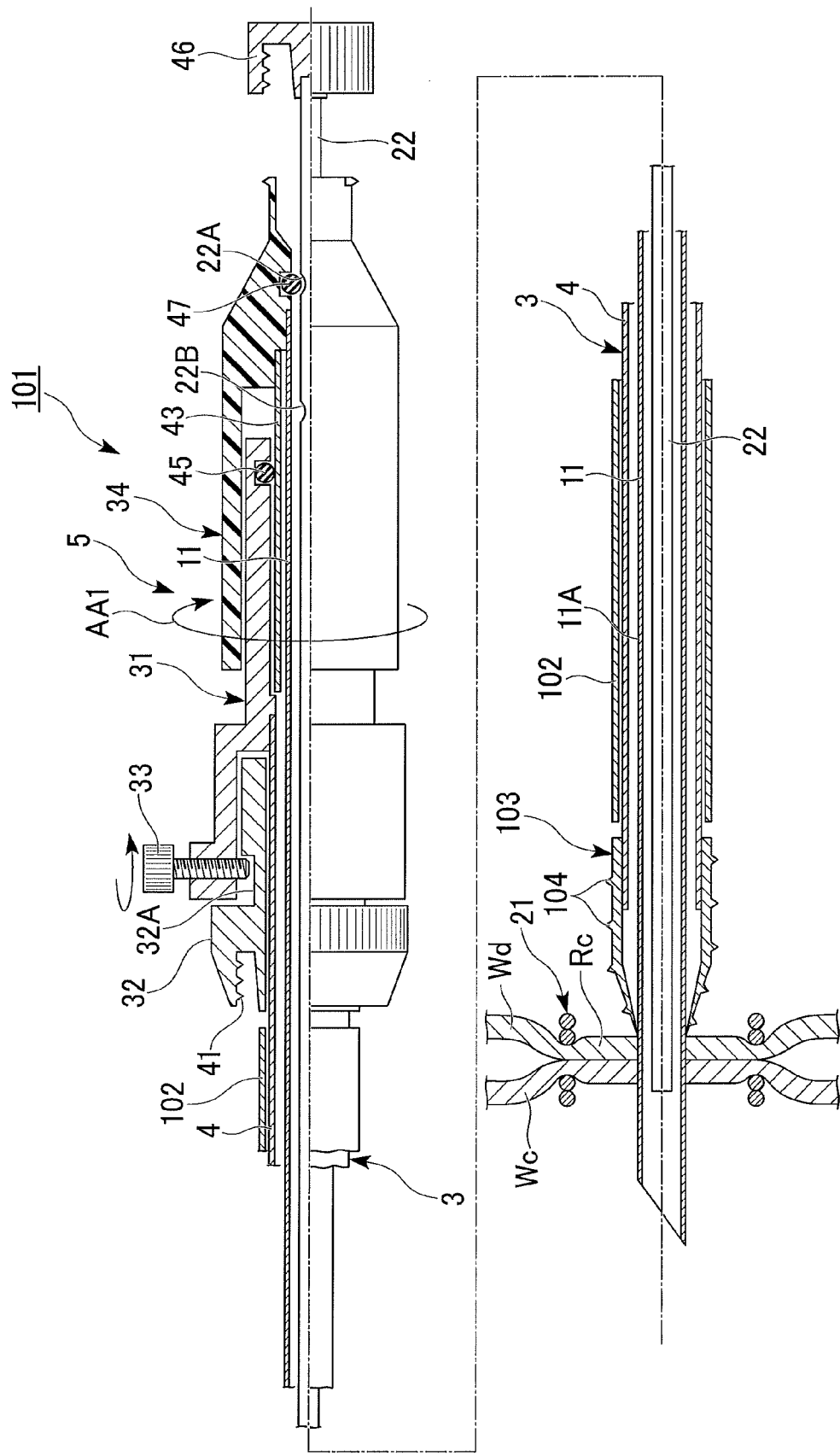
FIG. 43 shows the deployed section piercing the location where the tissue fastening tool is detained, and the stent pressing against a tissue.

As shown in FIG. 43, the area Rc fastened by the tissue fastening tool 21 is pierced by the deployed section 11A, and the front end of the stent 103 is deployed to the tissue. At this stage, the stylet 22 is slightly pulled back beforehand, and the incisive front end of the deployed section 11A is used to pierce the area Rc.

The securing screw 33 on the side of the operation part 5 is loosened slightly. The operation part body 31 is rotated around the axial direction with respect to the connector 32 in the direction shown by the arrow AA1. The sheath 4 fixed to the operation part body 31 rotates, and the stent 103 friction fitted to it also rotates. Thread 104 is formed on the outer periphery of the stent 103. If the stent 103 is rotated while pressing it against the duodenum wall Wd, the stent 103 is screwed into the duodenum wall Wd and the common bile duct wall Wc using the through hole formed by the deployed section 11A as a guide. At this stage, by keeping the stylet 22 pushed in completely, the front end of the stylet 22 protrudes slightly from the front end of the deployed section 11A; therefore, the body cavity tissues are not damaged by the incisive front end of the deployed section 11A.

Figure 44:
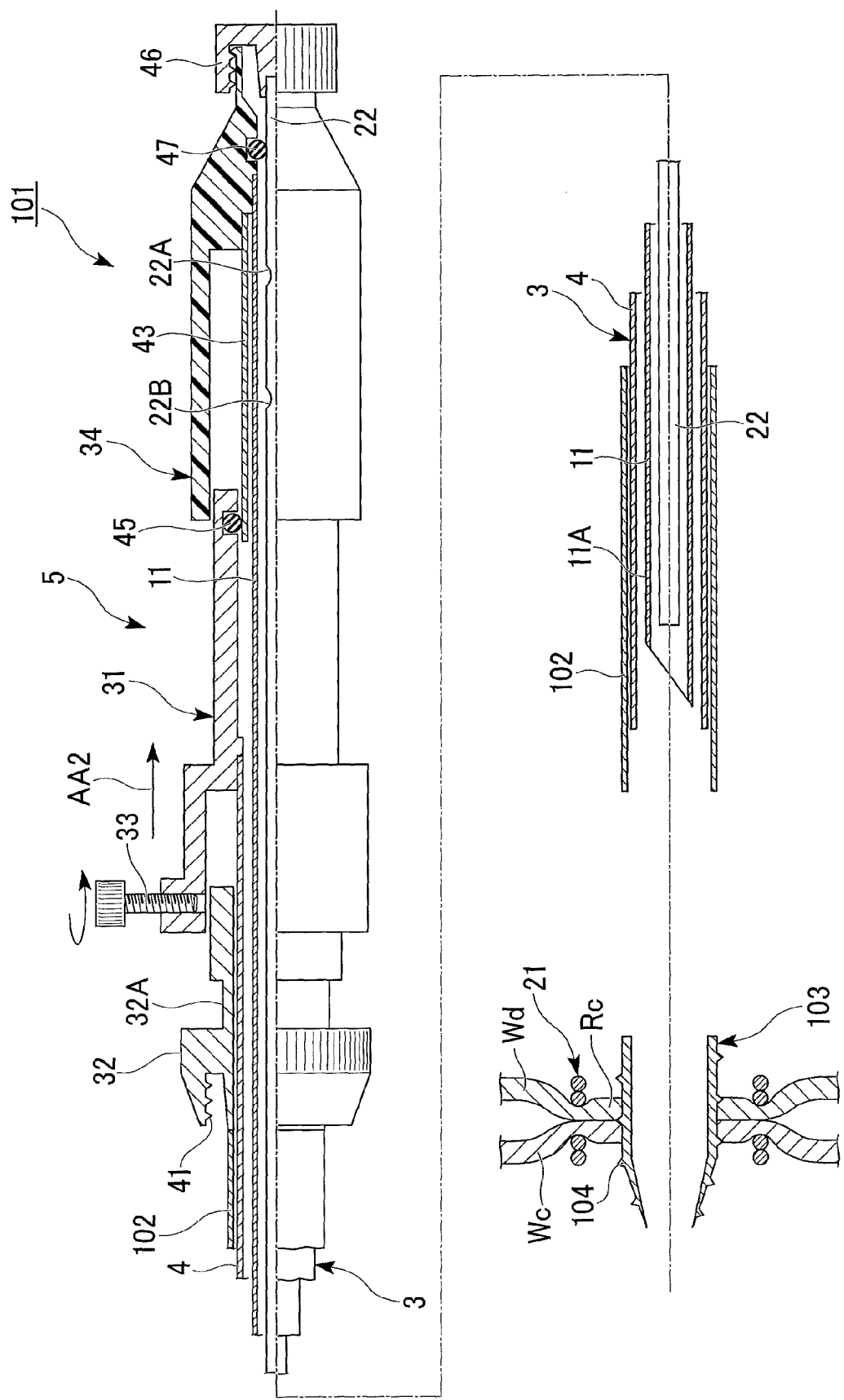
FIG. 44 shows the applicator retracted after a stent has been twisted into the tissue.

When the stent 103 is adequately screwed into the duodenum wall Wd and the common bile duct wall Wc, and the common bile duct Cd and the duodenum Dd are linked, the stent 103 is separated from the applicator 101. Initially, the deployed section 11A is pulled back and stored in the sheath 4. The securing screw 33 is further loosened such that the operation part body 31 becomes movable in the axial direction after crossing the groove 32A of the connector 32. As shown by the arrow AA2 in FIG. 44, the operation part body 31 is pulled away from the connector 32, and the sheath 4 is retracted. The pusher tube 102 is in contact with the connector 32 and it does not retract. Since the pusher tube 102 does not move, the stent 103 disposed at the front end of the pusher tube 102 also does not move from its position. As a result, the friction fit of the stent 103 and the sheath 4 is released, and only the stent 103 is detained. The bile will thus drain through the route ensured by the stent 103 from the common bile duct Cb to the duodenum Dd.

Figure 45:
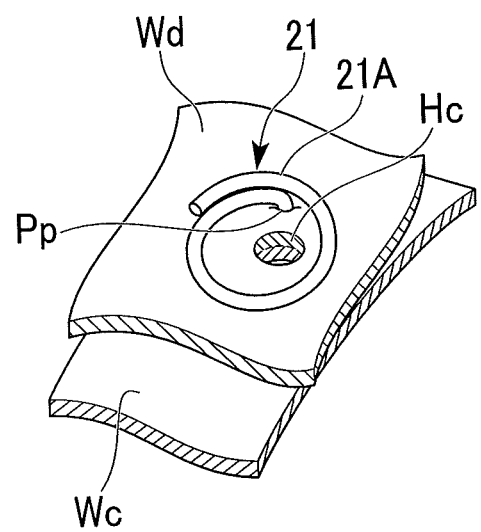
FIG. 45 shows the bile drainage opening formed after detaining the tissue fastening tool.
Figure 46:
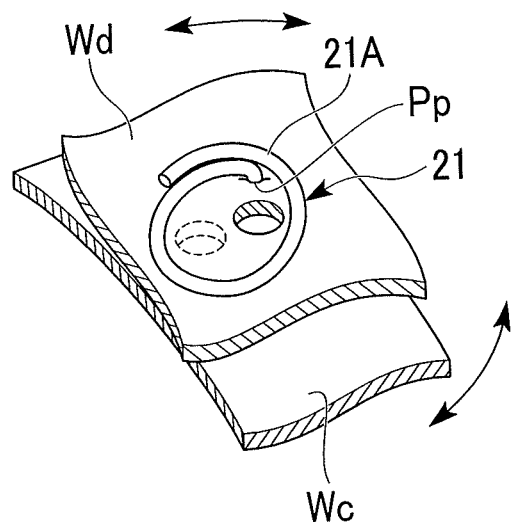
FIG. 46 is an explanatory drawing showing the rotation of duodenum wall and common bile duct wall, and the misalignment of the drainage opening.

As shown in FIG. 45, the duodenum wall Wd and the common bile duct wall Wc are fastened by the tissue fastening tool 21. When the bile drain opening is formed by the anastomosis hole Hc penetrating both walls Wd and Wc, the duodenum Dd and the common bile duct Cb may rotate, as shown in FIG. 46, around the center at point Pp through which the element wire 21A penetrates the tissue. In this case, the positions of the bile drain openings punctured in each of the two walls Wd and Wc may become misaligned, and bile drainage cannot take place. When the stent 103 is made to penetrate the walls Wd and Wc, the positional relationship between the duodenum Dd and the common bile duct Cb becomes stable, thereby stable bile drainage opening can be ensured.

Moreover, the stent 103 can be easily inserted in the tissue because its front end has a reduced diameter. The stent 103 can be screwed in easily but it does not come off easily because a ridged thread 104 is formed on the outer periphery of the stent 103. Either a fine, the reduced diameter of the front end or thread 104 may be provided, or both may not be provided.

Figure 47:
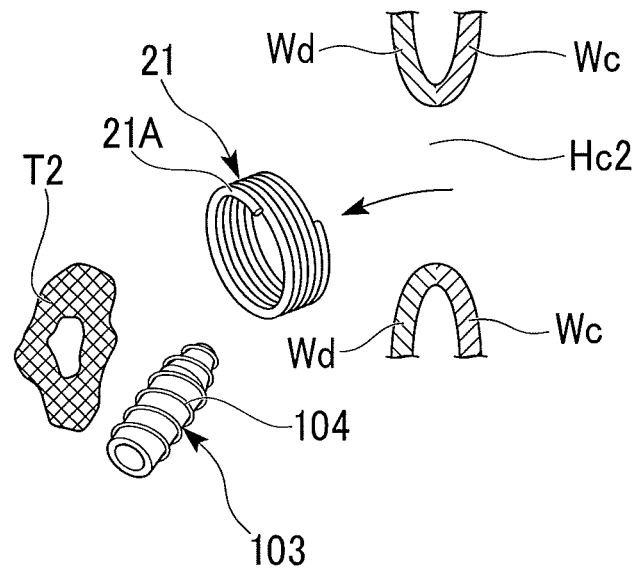
FIG. 47 shows the state when the tissue fastening tool, stent, and necrotized tissue have fallen into the duodenum side.

When the fastening force of the tissue fastening tool 21 is large, as shown in FIG. 47, the necrotized tissue T2, and the tissue fastening tool 21 and stent 103 fall off, and the fistulous opening Hc2 is formed. In this embodiment also, long term patency of the fistulous opening Hc2 for bypass is possible because the tissue fastening tool 21 and the stent 103 fall off.

Figure 48:
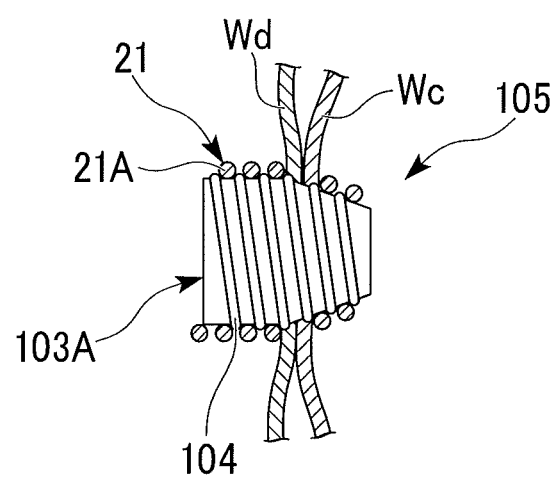
FIG. 48 shows the aligned condition of the stent screw pitch and coil pitch of the tissue fastening tool.

The coil pitch of the tissue fastening tool 21 and the pitch of the thread 104 may be made to substantially coincide, as in the stent 103A shown in FIG. 48. The stent 103 is fitted into the tissue fastening tool 21, so fall-off can be prevented further. In this case, the diameter at one end of the detention tool 105 is generally large, while that at the other end is small. When the tissue is necrotized, it falls off into the large diameter side, so the large diameter side is detained such that it is disposed in the duodenum Dd.

Figure 49:
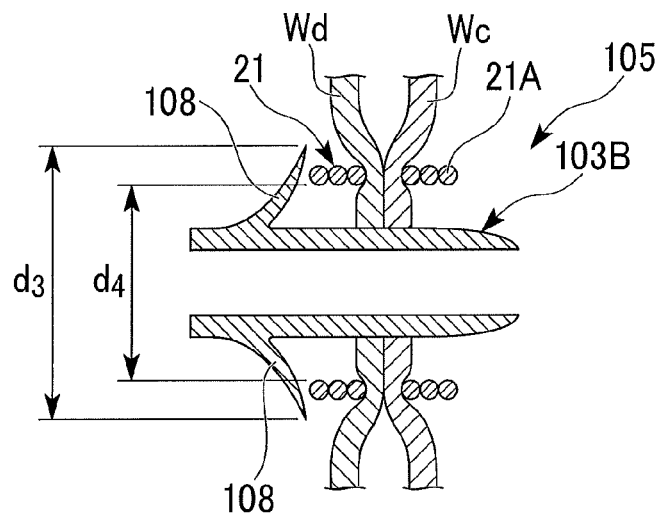
FIG. 49 shows the stent with flap.

As shown in FIG. 49, it is preferable to provide at least one flap 108 on the side of one end of the stent 103B. The width d3 with the flap 108 in the open condition is larger than the inside diameter d4 of the coil of the tissue fastening tool 21. The detention tool 105 falls off in the direction in which the flap 108 is provided. The present invention is not limited to this flap 108, and a convex part such as a flange may be provided instead.

(Seventh Embodiment)

Figure 50:
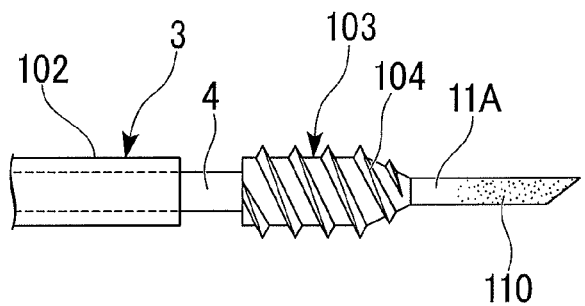
FIG. 50 shows the deployed section processed for ultrasonic wave reflection.

As shown in FIG. 50, the front end of the deployed section HA may be processed for ultrasonic wave reflection. The surface of this processed part 110 is roughened by dimples or by sand blasting, so as to diffuse the reflection of ultrasonic waves. During the procedure, the amount pierced by the deployed section 11A can be easily confirmed by ultrasonic wave observation.

The processed part 110 can also be used in the applicator 1 in which stent 103 and pusher tube 102 are not provided.

(Eighth Embodiment)

Figure 51:
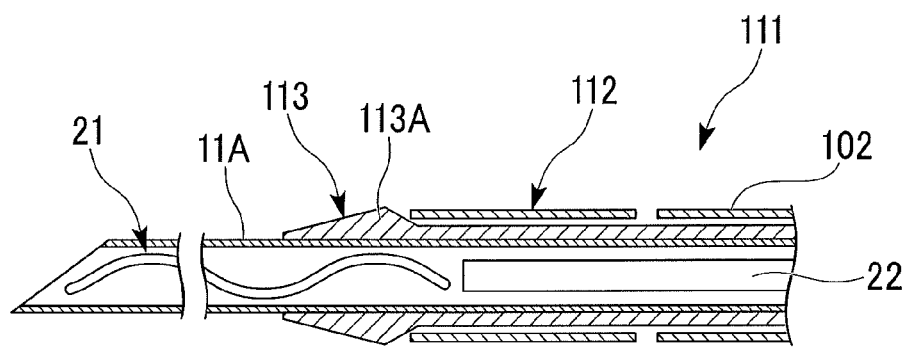
FIG. 51 is an explanatory drawing of the mode of using the dilator.
Figure 52:
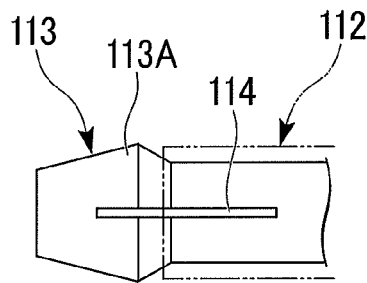
FIG. 52 is an external view of the dilator.

As shown in FIG. 51, the applicator 111 is provided with a dilator 113 to assist in inserting the stent 112 in the tissue. The dilator 113 is of cylindrical shape such that the deployed section 11A can pass through. The front end has a convex part 113A that protrudes in the direction of the enlarged diameter. The front end side and the base end side of the convex part 113A are both inclined. As shown in FIG. 52, at least one slit 114 is formed in the axial direction.

When the detention tool 105 is inserted in the body, the convex part 113A of the dilator 113 becomes a stopper and prevents the stent 112 from falling off. The deployed section 11A is disposed on the inside of the dilator 113 and it prevents deformation of the dilator 113. Therefore, the stent 112 does not move by crossing over the convex part 113A.

Similar to the embodiment mentioned above, when the common bile duct Cb is fixed to the duodenum Dd by the tissue fastening tool 21, a through hole is formed by the deployed section 11A in the area Rc fastened by the tissue fastening tool 21, and the dilator is advanced. The dilator 113 enters the common bile duct Cb while widening the through hole. When the front end of the stent enters the common bile duct Cb, the deployed section 11A is retracted and pulled out from the tissue. The deployed section 11A is retracted toward the base end side passing the convex part 113A of the dilator 113.

The pusher tube 102 is pushed to push out the stent 112 so that it crosses over the convex part 113A of the dilator 113. At this stage, the deployed section 11A is not on the inside of the dilator 113. The dilator 113 deforms in the direction of the reduced diameter with the slit 114 as the starting point, and allows the stent 112 to move. When the detention of the stent 112 is complete, the applicator 111 is pulled out together with the entire dilator 113.

Figure 53:
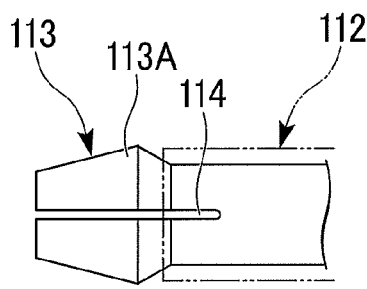
FIG. 53 shows an example of modification of the dilator.

As shown in FIG. 53, the slit 114 of the dilator 113 may be opened up to the front end. The front end part of the dilator 113 becomes more deformable, and the stent 112 becomes more easy to push out.

(Ninth Embodiment)

Figure 54:
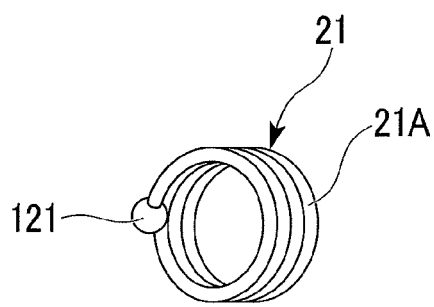
FIG. 54 is an external view of the tissue fastening tool with a grasping part.
Figure 55:
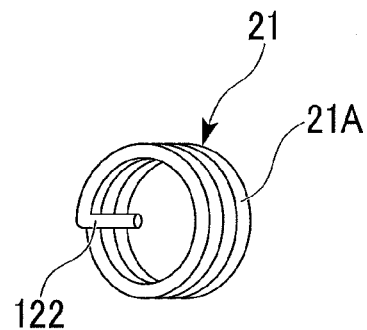
FIG. 55 is an external view of the tissue fastening tool with a grasping part.
Figure 56:
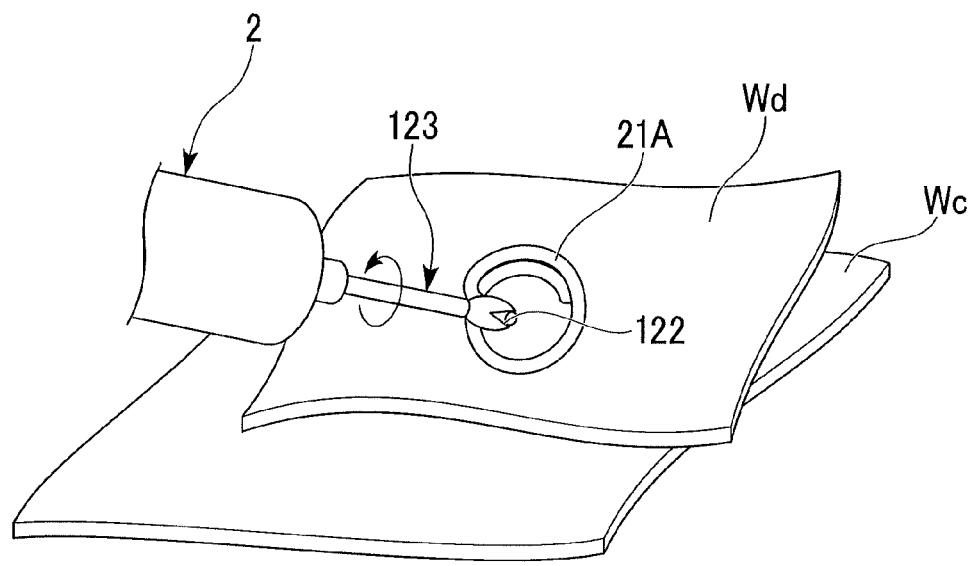
FIG. 56 shows the recovery operation of the tissue fastening tool using a grasping forceps.

As shown in FIG. 54 and FIG. 55, the tissue fastening tool 21 has grasping parts 121 and 122 formed at the ends of the element wire 21A. These grasping parts 121 and 122 become the starting points for removal of the tissue fastening tool 21. For example, as shown in FIG. 56, if the grasping part 122 is held by the grasping forceps 123 through the endoscope 2 and rotated, the tissue fastening tool 21 wound in coil shape can be easily pulled out from the tissue. When they are to be used in combination with the stent 103, the grasping parts 121 and 122 are formed at positions and of sizes that do not interfere with the stent 103.

(Tenth Embodiment)

Figure 57:
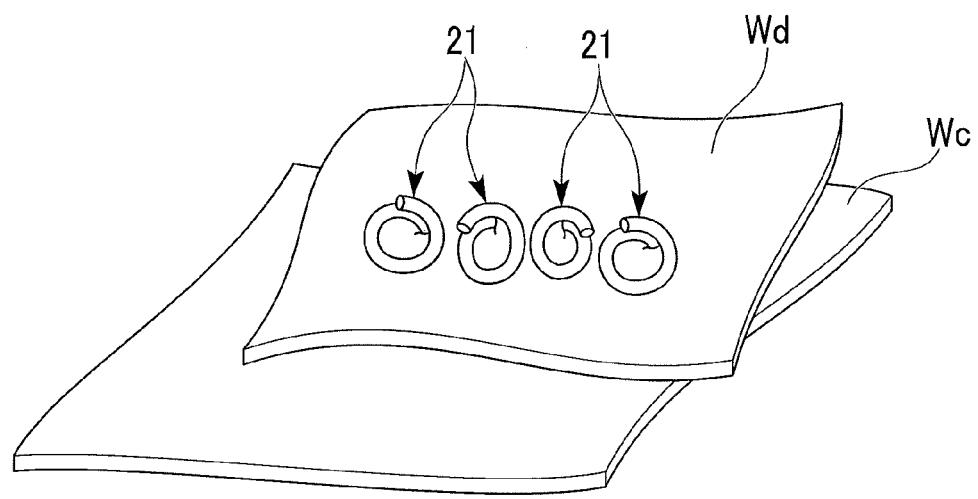
FIG. 57 shows a plurality of tissue fastening tools detained adjacent to each other.

As shown in FIG. 57, a plurality of tissue fastening tools 21 are detained in the tissue in a straight line. The tissue fastening tool 21 used is one in which the fastening force can necrotize the tissue. If applicator 1 is used, the tissue fastening tool 21 can be disposed at the desired position, and a plurality of tissue fastening tools 21 can be brought in proximity to each other and disposed. Accordingly, when each tissue fastening tool 21 falls off together with the tissue that it necrotized, a continuously long hole is formed in the direction in which the tissue fastening tools 21 are arrayed.

Figure 58:
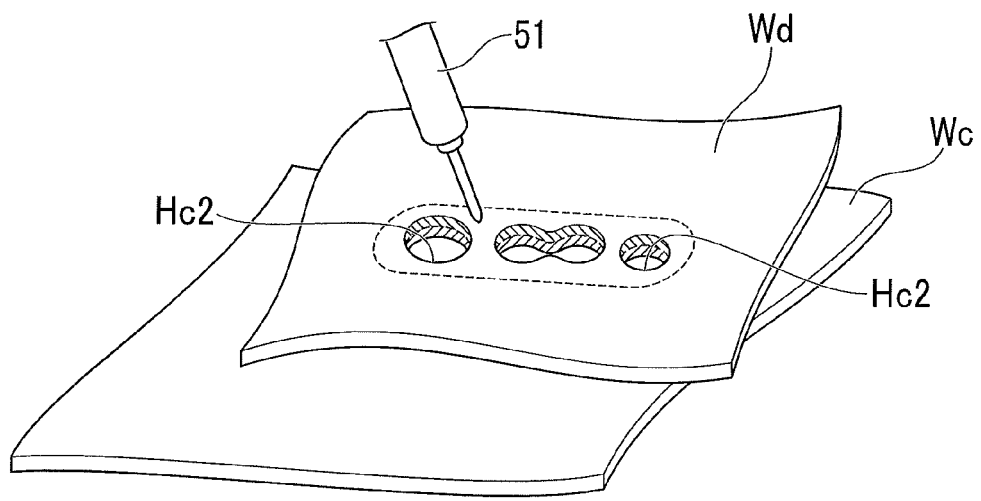
FIG. 58 shows the procedure for joining fistulous openings using a high-frequency knife after the tissue fastening tools has fallen off.
Figure 59:
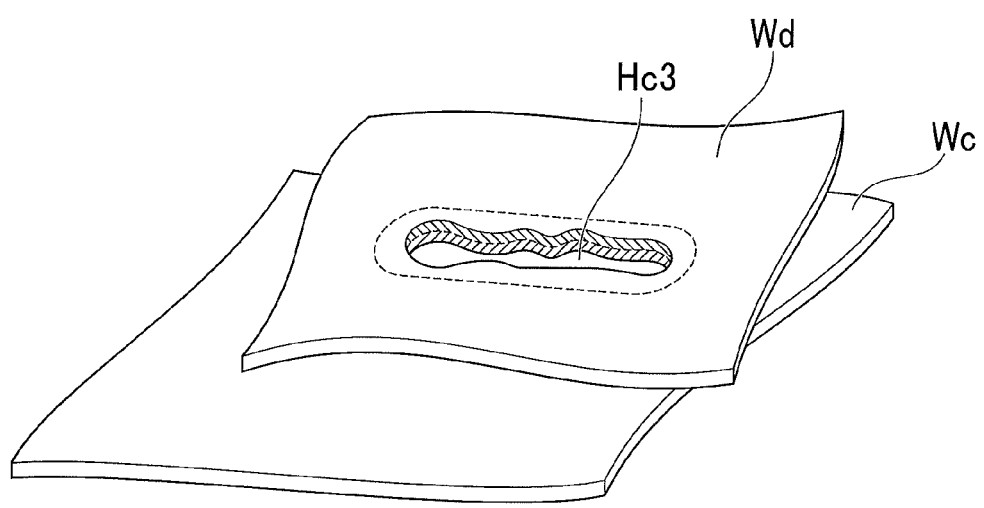
FIG. 59 shows an elongated hole formed by joining the fistulous openings.

As shown in FIG. 58, if the fistulous openings Hc2 formed by the tissue fastening tool 21 are not linked, the high-frequency knife 51 is used to dissect the coalesced portions. The area around the fistulous opening Hc2 becomes the coalesced range shown by dotted line in FIG. 58. Even if dissection is performed within the coalesced range, the bile does not leak from between tissue and tissue. As shown in FIG. 59, a continuous long hole Hc3 can be formed. The long hole Hc3 is not limited to a straight line shaped hole.

Figure 60:
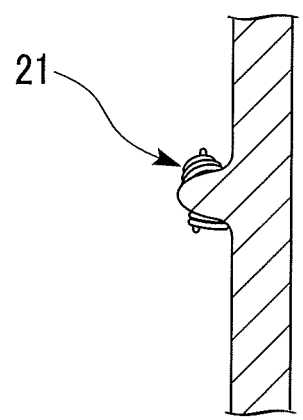
FIG. 60 shows tissue fastening tool detained in one tissue and distended.

The preferred embodiments have been described as above. However, the present invention is not limited to the descriptions above; they are limited only by the scope of claims appended here. The tissues fixed by the tissue fastening tool or detention tool in each of the embodiments are not limited to two separate tissues or organs. The deployed section 11A is passed through all layers of tissues sequentially when fixing two tissues, but when one tissue is to be fixed, a part of the layers are penetrated. As shown in FIG. 60, manipulation may be performed so as to distend the tissue with the center as the location that is partially penetrated.

What is claimed is:

1. A tissue fastening system comprising:
an endoscope including a connector and an instrument channel,
an applicator configured to be connected to the connector of the instrument channel of the endoscope when inserted into the instrument channel, and
a tissue fastening tool formed of an elastic wire, the tissue fastening tool including:
a first part having a plurality of first loops, the first part being formed from a portion of the elastic wire including one end of the elastic wire, the first part being formed around a longitudinal axis of the plurality of first loops, the first part having a restoring force enabling an entire circumference of two adjoining first loops of the plurality of first loops to abut each other, each of the plurality of first loops having a same winding outer diameter from one end of the first part to an other end of the first part; and
a second part formed by winding an other part of the elastic wire including an other end of the elastic wire, the second part being formed around the longitudinal axis of the plurality of first loops, the second part having a second loop which has an inner diameter larger than the winding outer diameter of the plurality of first loops,
wherein the applicator includes:
a flexible sheath that is configured to be inserted into an alimentary tract through a natural orifice;
a needle tube that includes a sharp end provided on a distal end thereof and a lumen which is extended inside the needle tube along a longitudinal axis of the flexible sheath, the needle tube being configured to be freely advanced or retracted along the longitudinal axis of the flexible sheath;

a pusher that is configured to push the tissue fastening tool housed in the needle tube, wherein the tissue fastening tool is housed in the needle tube such that the one end of the elastic wire is located on a distal opening side of the needle tube and the other end of the elastic wire is located at a pusher side in the needle tube, and the pusher is configured to push the other end of the elastic wire, and wherein the first part is configured to be released from the needle tube by pushing the other end of the elastic wire with the pusher, and wherein when the two adjoining first loops of the plurality of first loops are released from the needle tube the adjoining first loops are configured to clamp a tissue held therebetween so as to necrotize the tissue by the restoring force.

2. The tissue fastening system according to claim 1, wherein the one end of the elastic wire or the other end of the elastic wire is chamfered.

3. The tissue fastening system according to claim 1, wherein the one end and the other end of the elastic wire have a substantial spherical shape of diameter larger than a diameter of the elastic wire.

4. The tissue fastening system according to claim 1, wherein the one end and the other end of the elastic wire are folded back.

5. The tissue fastening system according to claim 1, wherein the one end and the other end of the elastic wire are folded back so as to enable grasping.

6. The tissue fastening system according to claim 1, wherein the tissue fastening tool is configured to detach from the tissue toward the other end of the elastic wire after the tissue held between the two adjoining first loops is necrotized.

7. The tissue fastening system according to claim 1, wherein the pusher is capable of advancing or retracting relative to the tissue fastening tool housed in the needle tube in a state that the pusher is disposed separated from a proximal end of tissue fastening tool.

8. The tissue fastening system according to claim 1, wherein the one end of the elastic wire constituting the first part is configured to be pushed out from the needle tube at first by pushing the other end of the elastic wire constituting the second loop by the pusher and the other end of the elastic wire constituting the second part is configured to be pushed out from the needle tube after all of the plurality of first loops are pushed out from the needle tube.

* * * * *